(12) United States Patent
Yenugonda et al.

(10) Patent No.: US 9,408,848 B2
(45) Date of Patent: Aug. 9, 2016

(54) FLUORESCENT CDK INHIBITORS FOR TREATMENT OF CANCER

(75) Inventors: Venkata Mahidhar Yenugonda, McLean, VA (US); Milton L. Brown, Brookeville, MD (US)

(73) Assignee: Georgetown University, Washington, DC (US)

( * ) Notice: Subject to any disclaimer, the term of this patent is extended or adjusted under 35 U.S.C. 154(b) by 344 days.

(21) Appl. No.: 13/059,180

(22) PCT Filed: Aug. 17, 2009

(86) PCT No.: PCT/US2009/054093
§ 371 (c)(1),
(2), (4) Date: May 6, 2011

(87) PCT Pub. No.: WO2010/019967
PCT Pub. Date: Feb. 18, 2010

(65) Prior Publication Data
US 2011/0269178 A1    Nov. 3, 2011

Related U.S. Application Data

(60) Provisional application No. 61/089,500, filed on Aug. 15, 2008.

(51) Int. Cl.
| | | |
|---|---|---|
| *C12Q 1/34* | (2006.01) | |
| *A61K 31/52* | (2006.01) | |
| *A61K 31/4164* | (2006.01) | |
| *A61K 49/00* | (2006.01) | |
| *C07D 209/14* | (2006.01) | |
| *C07D 233/72* | (2006.01) | |
| *C07D 317/26* | (2006.01) | |
| *C07D 473/16* | (2006.01) | |

(52) U.S. Cl.
CPC .............. *A61K 31/52* (2013.01); *A61K 31/4164* (2013.01); *A61K 49/0021* (2013.01); *A61K 49/0052* (2013.01); *C07D 209/14* (2013.01); *C07D 233/72* (2013.01); *C07D 317/26* (2013.01); *C07D 473/16* (2013.01)

(58) Field of Classification Search
CPC .............. A61K 31/52; A61K 31/4164; A61K 49/0021; A61K 49/0052; C07D 209/14; C07D 317/26; C07D 473/16
See application file for complete search history.

(56) References Cited

U.S. PATENT DOCUMENTS

| | | | | |
|---|---|---|---|---|
| 5,274,082 A | * | 12/1993 | Seri et al. ................. | 534/16 |
| 6,294,667 B1 | | 9/2001 | Jackson | |
| 6,573,044 B1 | * | 6/2003 | Gray et al. .................. | 506/10 |
| 2002/0016329 A1 | * | 2/2002 | Imbach et al. ............... | 514/261 |
| 2002/0146371 A1 | * | 10/2002 | Li et al. ...................... | 424/1.73 |
| 2002/0156277 A1 | | 10/2002 | Fick | |
| 2003/0092565 A1 | | 5/2003 | Chaudhari | |
| 2003/0176677 A1 | | 9/2003 | Lin | |
| 2004/0034224 A1 | | 2/2004 | Hammarstrom | |
| 2005/0009846 A1 | | 1/2005 | Fischer | |
| 2005/0124808 A1 | | 6/2005 | Miller | |
| 2005/0153371 A1 | * | 7/2005 | Grotzfeld et al. ............ | 435/7.5 |
| 2006/0229330 A1 | | 10/2006 | Bartkovitz | |
| 2007/0049603 A1 | | 3/2007 | Miknis | |

FOREIGN PATENT DOCUMENTS

| | | | |
|---|---|---|---|
| GB | 2334578 A | * | 8/1999 |
| WO | 9934018 | | 7/1999 |
| WO | WO 02076402 A2 | * | 10/2002 |
| WO | 03002565 | | 1/2003 |
| WO | WO 2007064759 A2 | * | 6/2007 |

OTHER PUBLICATIONS

Rosania et al. Proc. natl. Acad. Sci. USA (1999) 96: 4797-4802.*
Knockaert et al. Chem. Biol. (2000) 7: 411-422.*
Defintion of composition downloaded from www.dictionary.com/browse/composition on Dec. 26, 2014.*
Chang, et al., "Synthesis and application of functionally diverse 2,6,9-trisubstituted purine libraries as CDK inhibitors", Chem. Biol., 6:361-75 (1999).
Chu, et al., "Discovery of [4-Amino-2-(1-methanesulfonylplperidin-4-ylamino)pyrimidin-5,yl](2,3-difluoro-6-methoxyphenyl)methanone (R547), a potent and selective cyclin-dependent kinase inhibitor with significant in vivo antitumor activity", J. Med. Chem., 49:6549-60 (2006).
Cohen, et al., "Monitoring of chemotherapy-induced cell death in melanoma tumors by N,N'-Didansyl-L-cystine", Cancer Res. Treat., 6:221-34 (2007).
Collins and Garrett, "Targeting the cell division cycle in cancer: CDK and cell cycle checkpoint kinase inhibitors", Curr. Opin. Pharmacol., 5:366-73 (2005).
Damianovich, et al., "ApoSense: a novel technology for functional molecular imaging of cell death in models of acute renal tubular necrosis", Eur J. Nucl. Med., 33:281-91 (2006).
Davies, et al., "Structure-based design of a potent purine-based cyclin-dependent kinase inhibitor", Nat. Struct. Biol., 9:745-49 (2002).
Davies, et al., "Structure-based design of cyclin-dependent kinase inhibitors", Pharmacol Ther., 93:125-133 (2002).
Gray, et al., "Exploiting chemical libraries, structure, and genomics in the search for kinase inhibitors", Science, 281:533-38 (1998).
Harper and Elledge, "CDK inhibitors in development and cancer", Curr. Opin. Genet Dev., 6:56-64 (1996).
Huwe, et al., Small molecules as inhibitors of cyclin-dependent kinases Angew Chem. Int. Ed. Engl., 42:2122-38 (2003).
Knockaert, et al., "Pharmacological inhibitors of cyclin-dependent kinases", Trends Pharmacol Sci., 23:417-25 (2002).
Morgan, "Cyclin-dependent kinases: engines, clocks, and microprocessors", Annu. Rev Cell Dev. Biol., 13:261-91 (1997).

(Continued)

*Primary Examiner* — Susan Hanley
(74) *Attorney, Agent, or Firm* — Pabst Patent Group LLP

(57) ABSTRACT

Disclosed are molecules and their synthesis. The fluorescent moiety also facilitates screening, tracking, and pharmacodynamic studies of the drug in a biological system both in vitro and in vivo.

17 Claims, 9 Drawing Sheets

(56) References Cited

OTHER PUBLICATIONS

Figure 1A:
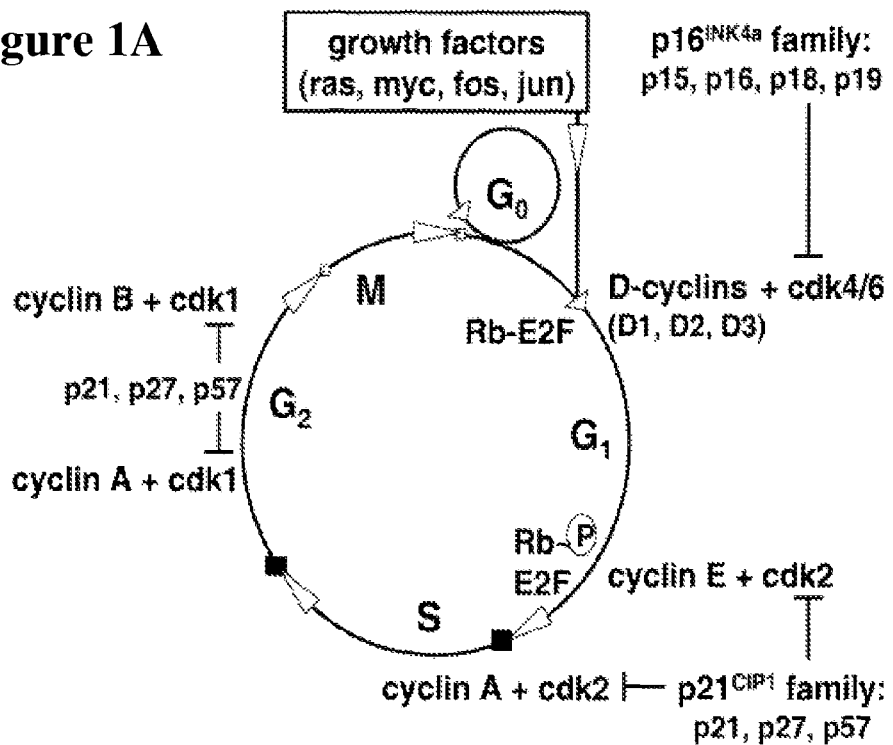

Nigg, "Cyclin-dependent protein kinases: key regulators of the eukaryotic cell cycle" Bioessays, 17:471-80 (1995).
Nigg, "Targets of cyclin-dependent protein kinases", Curr. Opin Cell Biol., 5:187-93 (1993).
Senderowicz, at al., "Phase I trial of continuous infusion flavopiridol, a novel cyclin-dependent kinase inhibitor, in patients with refractory neoplasms", J. Clin. Oncol., 16:2986-99 (1998).
Senderowicz, et al., "Preclinical and clinical development of cyclin-dependent kinase modulators", J. Natl. Cancer Inst., 92:376-87 (2000).
Senderowicz, "Small-molecule cyclin-dependent kinase modulators", Oncogene, 22:6609-6620 (2003).
Sharpiro, "Cyclin-dependent kinase pathways as targets for cancer treatment", J. Clin. Oncol., 24:1770-83 (2006).
Sherr, "Cancer cell cycles", Science, 274:1672-77 (1996).
Stearns, et al., "Dansylated estramustine, a fluorescent probe for studies of estramustine uptake and identification of intracellular targets", PNAS, 82:8483-87 (1985).
Summerer, at al., "A genetically encoded fluorescent amino acid", PNAS, 103:9785-89 (2006).
Vermeulen, et al., "The cell cycle: a review of regulation, deregulation and therapeutic targets in cancer", Cell Prolif., 36:131-49 (2003).

\* cited by examiner (A) INACTIVE  (B) PARTLY ACTIVE  C) Fully ACTIVE

*Molecular Biology of the cell, Fourth Edition   Fig17-17*

Figure 3A
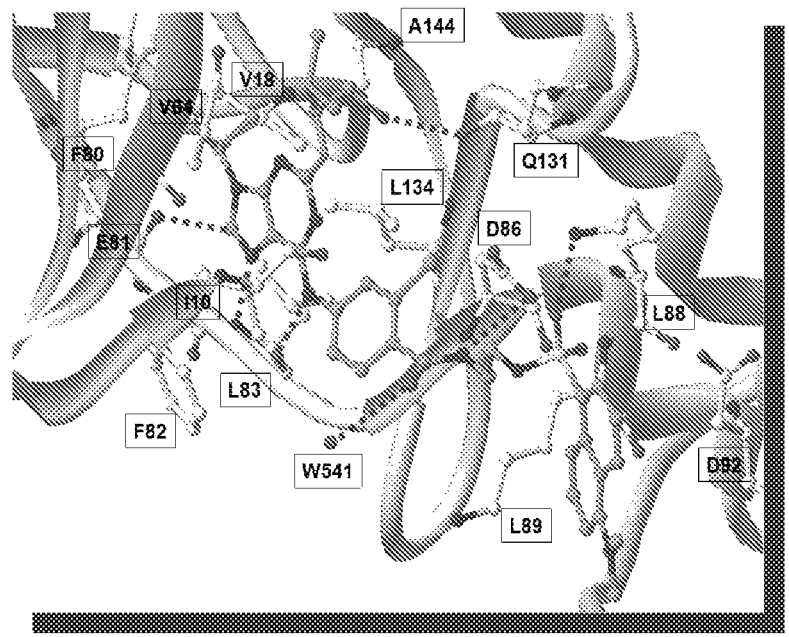
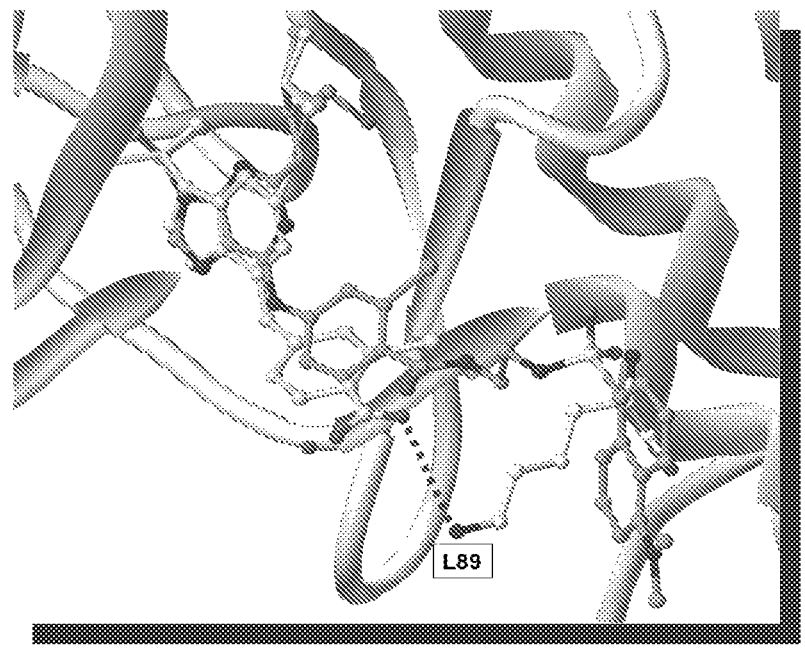
Figure 3B

MDA-MB-231

MCF-7

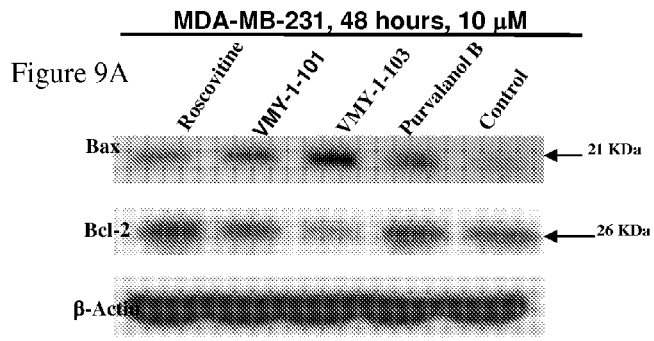
Figure 9A
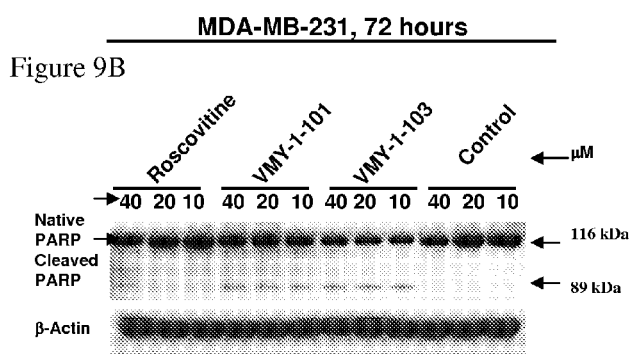
Figure 9B
Figure 9C
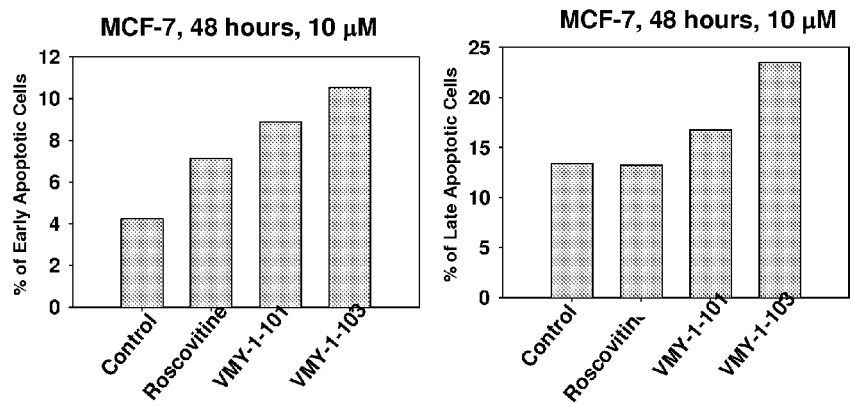

FLUORESCENT CDK INHIBITORS FOR TREATMENT OF CANCER

I. CROSS-REFERENCE TO RELATED APPLICATIONS

This application is a national phase filing under 35 U.S.C. 371 of PCT/US2009/054093 filed under the Patent Cooperation Treaty on Aug. 17, 2009, which claims benefit of and priority to U.S. Provisional Application Ser. No. 61/089,500, filed on Aug. 15, 2008, the contents of each being hereby incorporated by reference in their entirety.

II. BACKGROUND

The cyclin-dependent kinases (CDKs) are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p53, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of inhibits. A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer, and is herein incorporated by reference at least for material related to CDKs and cancer. CDK inhibitors are known. For example, flavopiridol (Formula I) is a nonselective CDK inhibitor that is currently undergoing human clinical trials (A. M. Sanderowicz et al, J. Clin. Oncol. (1998) 16, 2986-2999).

III. SUMMARY

Disclosed are methods and compositions related to protein kinases, their use and activities and molecules that bind them.

IV. BRIEF DESCRIPTION OF THE DRAWINGS

The accompanying drawings, which are incorporated in and constitute a part of this specification, illustrate several embodiments and together with the description illustrate the disclosed compositions and methods.

Figure 1B:
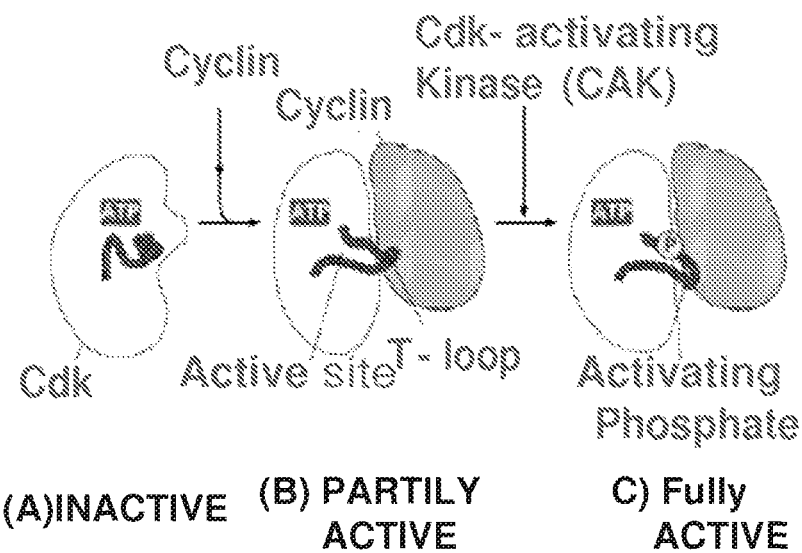

FIG. 1. shows an overview of a cell cycle and its interactions of cyclin dependent kinases (CDK's) and CDK regulation.

Figure 2A:
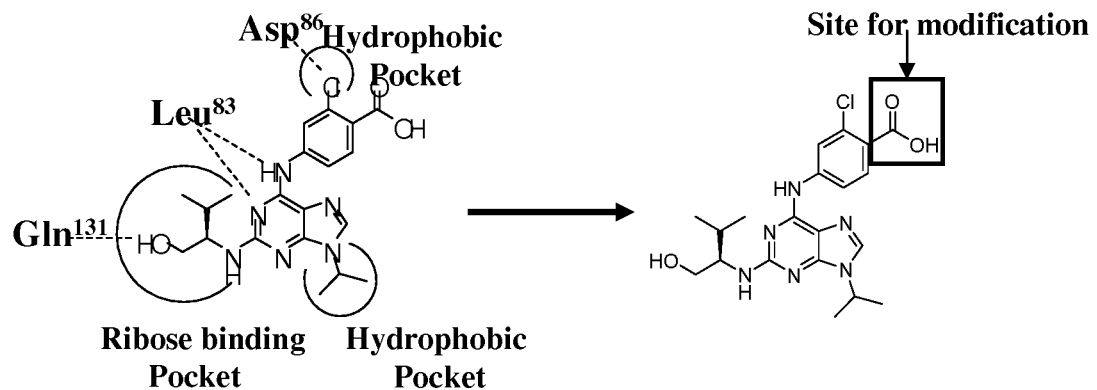

FIG. 2: Design Strategy for New class of fluorescent CDK molecules (A) and fluorescent purvalanol B analogues (B).

FIG. 3 shows the VMY-1-103 modeled in the ATP binding pocket of CDK2 (A): H-bond interactions are indicated by dotted lines (red) connecting the respective residue. The CDK2 is represented by ribbon model and residues interacting with VMY-1-103 shown by ball & stick model. VMY-1-103 is shown stick representation with their carbon atoms are colored green. (B) Overlay of VMY-1-103 with Purvalanol B (yellow).

Figure 4:
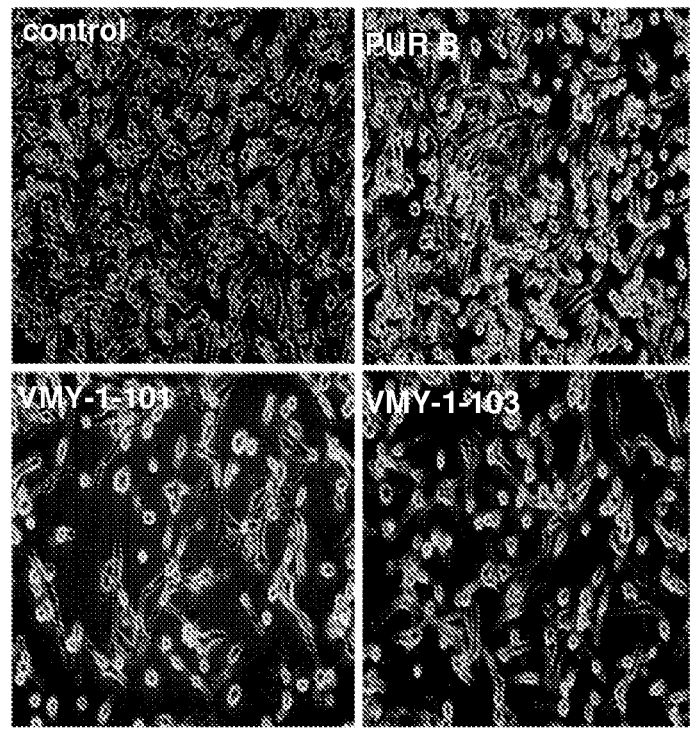
Figure 4:
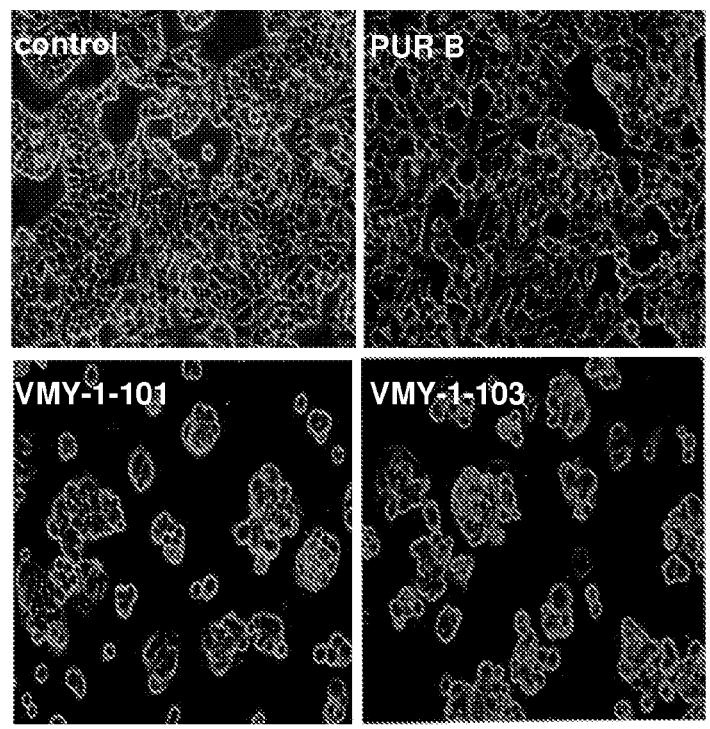

FIG. 4 shows morphological changes in human breast cancer cell lines after exposed with 10 µM of VMY compounds for 48 h. Morphological changes in human breast cancer cell lines after exposed with different compounds. Cells (3×105) were treated with 10 mM of Purvalanol B, VMY-1-101 and VMY-1-103 for 48 h. After treatment, media was removed and washed with PBS. Capture the images on olympus 1×71 inverted digital microscope system in the bright field magnification ×20.

Figure 5:
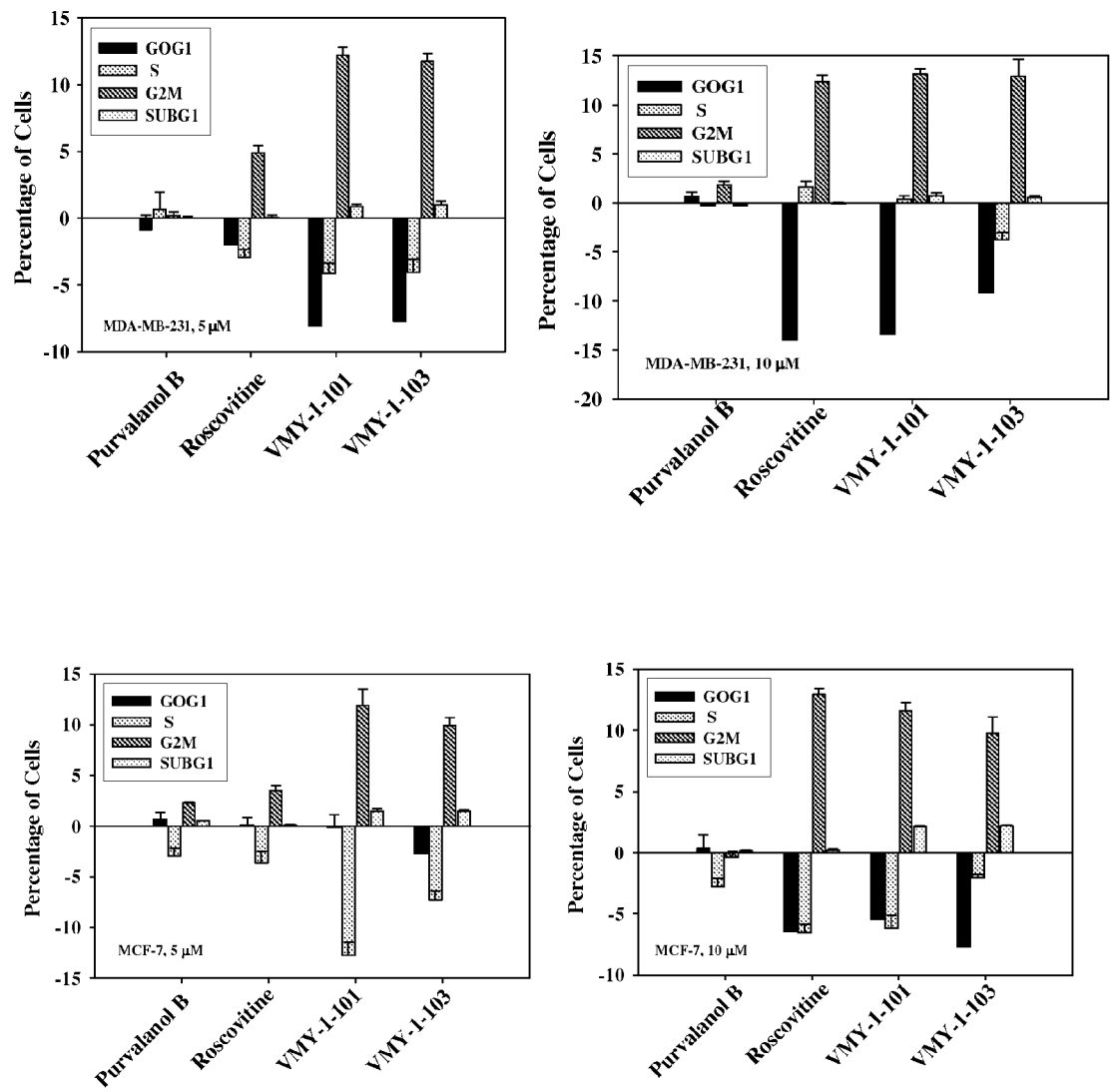

FIG. 5 summarizes the effect of VMY compounds on cell cycle distribution in breast cancer cells. VMY Compounds stops the cell cycle progression at G2/M phase. The details of description are as described in the example sections. The effect of compounds on cell cycle distribution: Asynchronised MDA-MB-231 cells were treated with 5 mM (A) and 10 mM (B) for 24 hours and similarly asynchronised MCF-7 cells were treated with 5 mM (C) and 10 mM (D) for 24 hours. Cell cycle distributions were determined by flow cytometry using propidium iodide staining of fixed cells (details as described in the experimental sections). The percentage of cells in each phase of cell cycle represents in the graph as subtracted values from untreated cells (Control). Results are represented as a mean of triplicate samples.

Figure 6:
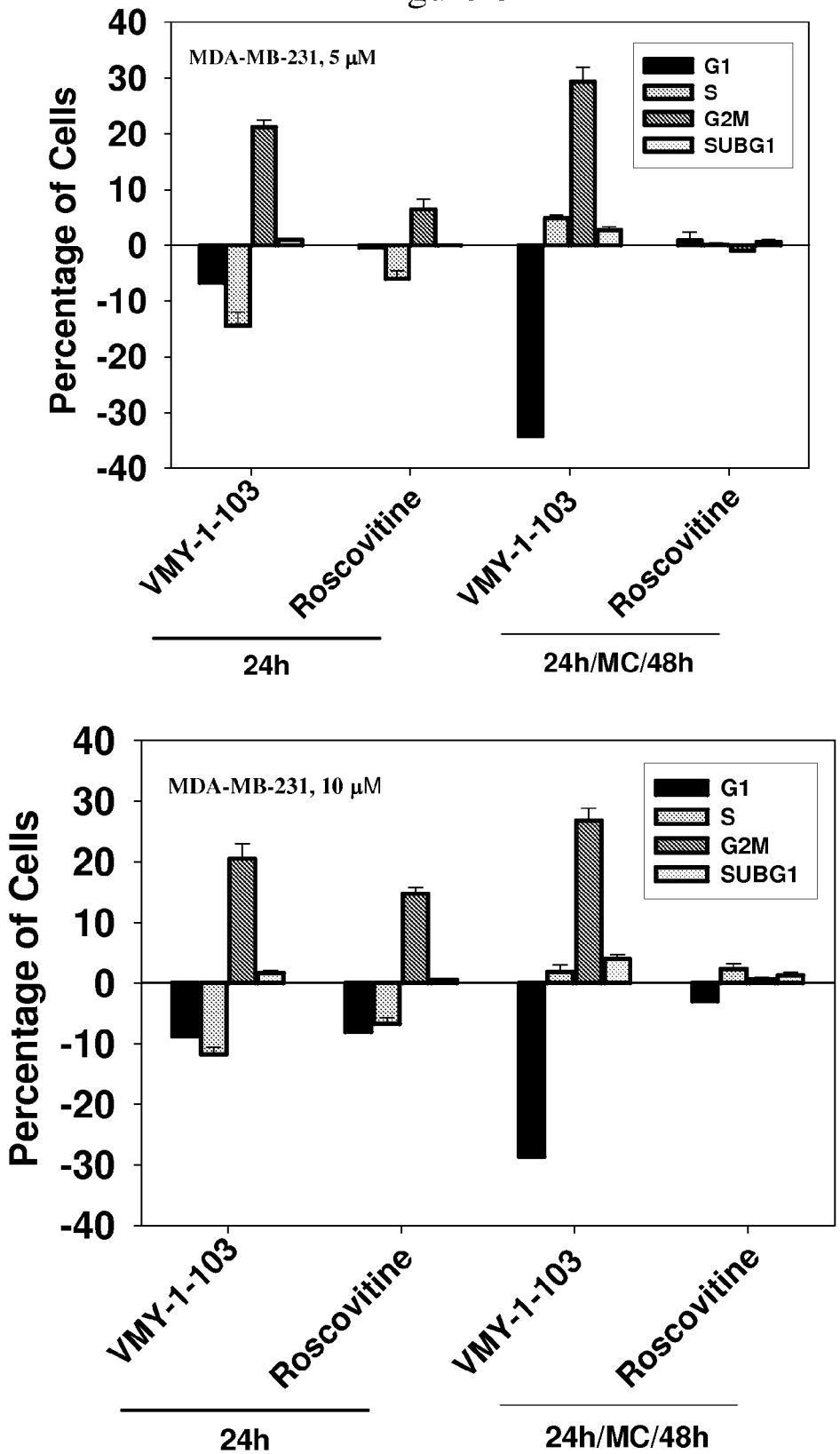

FIG. 6 summarizes the antiproliferative effect of VMY-1-103 is Irreversible in breast cancer cells. The details of description are as described in the example sections. Antiproliferative effect of VMY-1-103 is Irreversible/reversible: Exponentially growing MDA-MB-231 cells were treated with VMY-1-103 at 5 mM and 10 mM. Cells were treated for 24 h and additionally, after post-incubation for 48 h in a compound free media (24 h/MC/48 h). Cell cycle distributions were determined by flow cytometry using propidium iodide staining of fixed cells (details as described in the experimental sections). The percentage of cells in each phase of cell cycle represents in the graph as subtracted values from untreated cells (control). Results are represented as a mean of triplicate samples.

Figure 7:
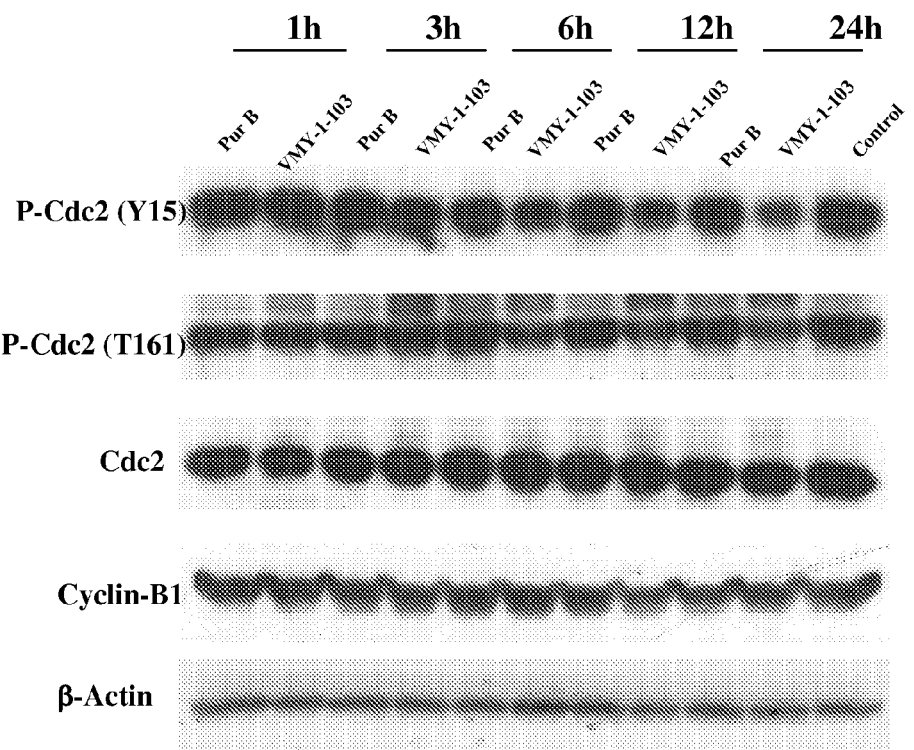
Figure 7:
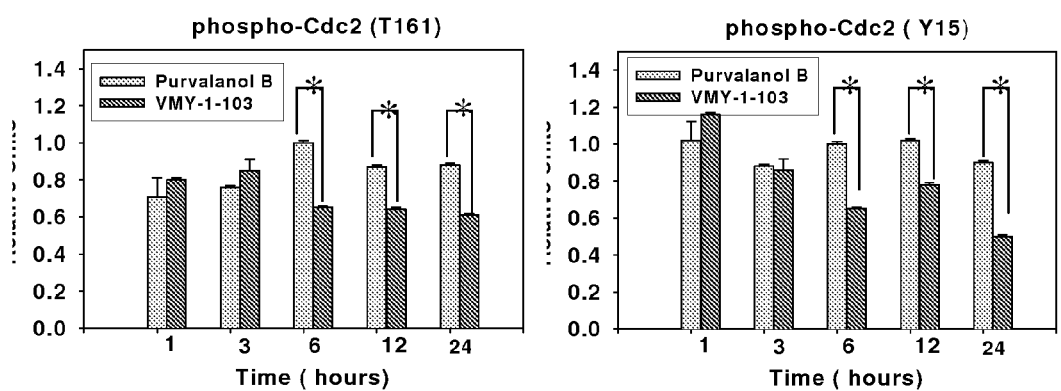

FIG. 7 provides the mechanism of action of VMY-1-103 in vitro conditions. VMY-1-103 decrease the phosphorylation level of G2/M checkpoint proteins which halts the cell cycle progression at G2/M phase. Mechanism of action of VMY-1-103 in vitro conditions. MDA-MB-231 cells treated with 10 mM of purvalanol B and VMY-1-103 at different time intervals, such as 1, 3, 6, 12 and 24 h and cellular protein was subjected to western blot analysis to analyze the phosphorylation status of Cdc2 substrates. Actin in each sample was employed as a standard. Below are shown quantification of bands of phospho-CDC2 (Y15), phospho-CDC2 (Y15), were performed using NIH image analysis normalized to actin. Data are expressed as mean±SD for three values.

Figure 8A:
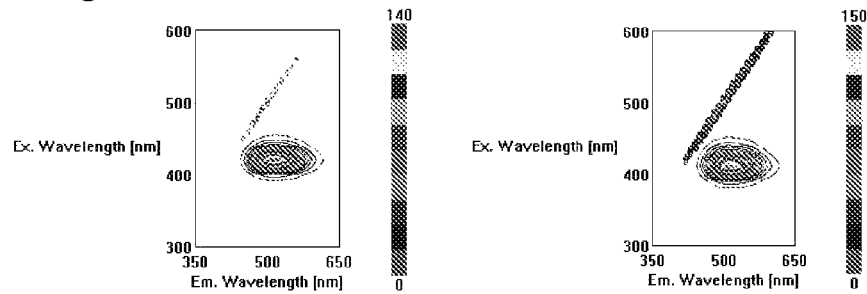

FIG. 8 Panel A shows the fluorescence spectrum of Dansyl ethylenediamine (Left, Excitation/Emission, 410/512 nm) and VMY-1-103 (Right, Excitation/Emission, 410/512 nm). Both compounds were dissolved in methanol and fluorescence spectrums were measured by fluorescent spectrophotometer. Panel B provides the intracellular localization of VMY Compounds. The compound was localized in the cytoplasmic compartments of the cells. The details of description are as described in the example sections. Confocal images of MDA-MB-231 (upper) and MCF-7 (Lower) of human breast cancer cell lines containing VMY-1-103. Cells (5×105) were treated with the 10 mM VMY-1-103 for 1 h. After treatment, cells were washed with PBS, fixed with 4% formaldehyde in PBS, stained with PI, and mounted on glass slides. The Zeiss LSM510/META/NLO live imaging multiphoton microscope was used to visualize the fluorescence with Magnification ×63. Excitation was at 720 nm and absorbance was read at bandpath filter of 480-520 nm. Panel C: Distribution of VMY-1-103 compare to Dansyl ethylenediamine towards Human Breast Tissue. VMY-1-103 has strong binding ability towards human breast tissue compare to dansylethylene diamine (Fluorophore) alone. Binding ability of VMY-1-103 compare to Dansyl ethylenediamine towards Human Breast Tissue. After epitode retrieval of human breast cancer tissue as mentioned in the materials and methods, exposed to 10 mM VMY-1-103 and Dansyl ethylenediamine for 1 h. After treatment, tissues were washed with water, mounted with aqua amount. Zeiss LSM510/META/NLO live imaging multiphotonmicroscope was used to visualize the fluorescence with Magnification ×63. Excitation was at 720 nm and absorbance was read at bandpath filter of 480-520 nm.

FIG. 9 provides the effects on the expression of apoptosis related proteins (Panel A and B) in response to compounds treatment.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

1. A, an the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Binding Affinity

The term binding affinity as used herein can be defined as two molecules interacting with a kd of at least $10^{-3}$, $10^{-4}$, $10^{-5}$, $10^{-6}$, $10^{-7}$, $10^{-8}$, or $10^{-9}$ M or tighter binding.

3. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

4. CDK Modulator

The term CDK modulator as used herein means a modulator of a cyclin-dependent kinase.

5. Complex

The term complex as used herein refers to the association of a compound with an ion channel or enzyme for which the compound has a binding affinity.

6. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

7. Chemistry a) Aldehyde

A reference herein to an aldehyde that has no alpha hydrogens mean an HC(═O)— group that is bonded to a carbon atom that has no covalent bond to a hydrogen atom. Non-limiting illustrative examples include alpha carbons for which each of the other three bonds is to a carbon atom, heteroatom or halogen atom; examples of such alpha carbons include that are part of aromatic, heteroaromatic, quaternary alkyl, and trihalomethyl substitutents.

b) Small Bulky Side Group

The term small bulky group as used herein with reference to an organic moiety refers to a hydrophobic substituent such as a halogen, $C_1$-$C_4$ organic, $C_1$-$C_4$ alkyl or dialkyl amino, $C_1$-$C_4$ alkoxy, $C_1$-$C_4$ sulfur moiety such as sulfyl or sulfoxyl or sulfonyl, wherein any of the organic, amino, alkoxy, or sulfur moiety may optionally be substituted with one or more halogens, methoxyl, methyl or dimethyl amino, or methyl sulfide residues.

c) $C_1$-$C_4$ Organic

The $C_1$-$C_4$ organic as used herein with respect to a substituent refers to a linear, branched or cyclical carbon residue that may be saturated or unsaturated, and may be substituted or unsubstituted as defined in this specification.

d) Close Proximity

The term close proximity as used herein with reference to a substituent relative to an aromatic or heteroaromatic ring herein refers to a location on the ring itself or on a position alpha, beta or gamma to the ring.

e) Small Bulky Group

The term small bulky group as used herein with reference to an organic moiety refers to a hydrophobic substituent such as a halogen, $C_1$-$C_4$ organic, $C_1$-$C_4$ alkyl or dialkyl amino, $C_1$-$C_4$ alkoxy, $C_1$-$C_4$ sulfur moiety such as sulfyl or sulfoxyl or sulfonyl, wherein any of the organic, amino, alkoxy, or sulfur moiety may optionally be substituted with one or more halogens, methoxyl, methyl or dimethyl amino, or methyl sulfide residues.

f) Facile Separation

The term "facile separation" as used herein with respect to stereoisomeric products refers to separation of the stereoisomers chromatographically to obtain one or both of the chiral forms in high purity in a single simple chromatographic step. For instance, obtaining by flash chromatography a stereoisomer with 90% or higher purity as determined by spectroscopic methods is a facile separation.

g) Substituted

The term "substituted" as used herein refers to an atoms or group of atoms substituted in place of a hydrogen atom on a linear, branched or cyclic organic compound or functional group. As used herein, the term substituent is employed without regard to whether the organic compound or functional group in its unsubstituted form comprises a heteroatom.

h) Lithiated Aryl

The term "lithiated" as used herein with respect to an aryl or heteroaryl group refers to an aryl or heteroaryl group having a negatively charged lone pair of electrons on the ring for which the counterion is a lithium cation.

i) Vinyl Anion

The term "vinyl anion" as used herein refers to the reactive intermediate [=C(:)-]$^-$, wherein a carbon having a double bond to a first neighboring carbon and a single bond to a second neighboring carbon furthermore has an unbonded lone pair of electrons that imparts to it a negative charge.

j) Heteroaryl Group

The term "heteroaryl group" as used herein refers to a functional group comprising at least one heteroatom in at least one aromatic ring.

k) Purine/Pyrimidine

The term "purine" or "pyrimidine" as used herein with respect to a ring system refers to a characteristic purine or pyrimidine structure, respectively, within that ring system.

l) Protected

The term "protected" as used herein has its usual and ordinary meaning in organic chemistry, and refers to a molecule or functional group that has been modified at one or more sites by reaction with a compound that may be readily removed to restore the original functional group, wherein the modified group selectively resists reaction with a chemical agent that is employed to react another site of the protected molecule. Illustrative protective groups and their chemistry are described in T. W. Green and P. G. M. Wuts, Protective Groups in Organic Synthesis, 3$^{rd}$ Ed., Wiley Interscience.

m) Unprotected

The term "unprotected" as used herein has its usual and ordinary meaning in organic chemistry, and refers to a molecule or functional group that remains unmodified or has been deprotected, such that one or more unprotected sites remain susceptible to or by deprotection become susceptible to reaction with a chemical agent in a particular step to which the molecule or functional group is subjected.

n) Moiety and Functional Group

The terms "moiety" and "functional group" as used herein are synonymous. The term functional group as used herein has its usual and ordinary meaning in organic chemistry, and refers to an interconnected group of atoms that is responsible for a characteristic chemical reaction of the molecule to which the group is bonded.

o) Hydrocarbon

The term "hydrocarbon" as used herein refers to an organic substituent or compound consisting entirely of hydrogen and carbon. As used herein the term hydrocarbon may refer to a substituent or compound that is of any size; linear, branched or cyclic; achiral, prochiral, chiral or racemic, aromatic, homoaromatic or saturated or unsaturated nonaromatic; and fully bonded or having a radical, electron lone pair, or empty orbital.

p) Amine Group

The term "amine group" as used herein has its usual and ordinary meaning in organic chemistry, and refers to a functional group having a basic nitrogen atom, wherein the nitrogen atom has a lone pair and a total of three covalent bonds, being covalently bonded to one or more hydrogen atoms and or to one or more organic moieties.

q) Carboxylic Acid

The term "carboxylic acid" as used herein refers to the functional group —C(=O)—OH. The term "alpha-hydroxy carboxylic acid" as used herein to the functional group >C(—OH)—C(=O)—OH.

r) Amide

The term "amide" as used herein refers to the functional group >N—C(=O)—.

s) Sulfamide

The term "sulfamide" as used herein refers to the functional group >N—C(=S)—.

t) Phosphoamid

The term "phosph(o)amid(e)" as used herein refers to amides of phosphoric acid and of its salts and esters, such as for the functional group >N—P(=O)(—O—)$_2$.

u) Reactive Moiety

The term "reactive moiety" as used herein refers to a moiety capable of condensation with a protected or unprotected group toward which it is reactive. Examples of reactive moieties include those susceptible to nucelophilic attack, such as moieties that can lose a leaving group such as a halide, a halogenated conjugate base of an organic acid, a tosylate, or a pyridinium functional group bonded to an acid moiety. Other examples of reactive moieties include nucleophiles, for instance, amine groups. Other examples of reactive moieties include those that have a carbonyl or other site at which nucleophilic attack by a second functional group can accomplish condensation. The term reactive moiety includes but is not limited to reactive moieties that are further substituted with another moiety such as a carboxylic acid, amide, sulfamide or phosphamide.

v) Acid Moiety

The term "acid moiety" as used herein refers to an acidic functional group such as —CO$_2$H, —SO$_3$H, —O—SO$_3$H, —SO$_2$H, —O—SO$_2$H, —PO$_3$H, —O—PO$_3$H, and the like.

w) Weinreb Amide

The term "weinreb amide" as used herein refers to refers to a N,O-dimethylhydroxamic acid. An illustrative but not exclusive weinreb amide is R—C(=O)—N(—CH$_3$)—O—CH$_3$ wherein R is an alkyl group x) Grignard Reagent The term "Grignard reagent" as used herein refers to magnesium halide R$_1$-MgX, wherein X represents F, Cl, Br or I, and wherein R$_1$ represents an organic moiety such as an aryl, alkyl, alkenyl or alkynyl compound, aralkyl, alkaryl, aralkenyl, alkenyl aryl, aralkynyl, alkynyl aryl, or substituted compound of one of those types.

y) Halogen

The term halogen as used herein with respect to substitution refers to a fluoro-, chloro-, bromo-, or iodo-substituent.

z) Halogenated Conjugate

The term halogenated conjugate base of an acid as used herein refers to conjugate bases of acids—or their use as residues for leaving groups—such as mono-, di-, tri-, and poly-halo alkyl acids, such as are familiar to the person of ordinary skill in the art for application as leaving groups and anions of very weak basicity. The fluoro and chloro derivatives are particularly widely used, as are —$CO_2^-$ and —$SO_3^-$ conjugate acids in these applications. The alkyl portion is commonly but not exclusively short chain alkyl acids, and longer residues such as fluoropolymer-substituted conjugate bases as well as aromatic structures such as halophenoxy residues are also contemplated within the scope of the invention.

aa) Heterocyclic Group

The term heterocyclic group as used herein refers to a ring structure having 4 to 8 members including at least one heteroatom and at least one carbon atom, wherein the structure is not heteroaromatic, and wherein the ring may be saturated or unsaturated, and may optionally be substituted by one or more: $C_1$-$C_4$ organic group; =O; ether, ester, carbonate, amine, amide, or urea of a $C_1$-$C_4$ organic group; any of which may optionally be substituted by a halogen.

bb) Lipophilic Side Chain

The term lipophilic side chain or lipophilc chain or lipohilic moiety and like terms as used herein refers to a side chain having lipophilic properties. The side chain or linker may be alkyl, alkenyl, alkynyl, or may be a polyether such as a polyethylene glycol or its alkyl ether, or polypropylene glycol or its alkyl ether, or a polyalkylamine, and or may have an ester, sulfoester, phosphoester, amide, sulfamide, or phosphoamide moiety in its backbone. A lipophilic side chain as referenced herein may be substituted by a halogen, $C_1$-$C_4$ organic group, $C_1$-$C_4$ ether, $C_1$-$C_4$ ester or sulfester or phosphoester, mono- or di-$C_1$-$C_4$ alkylamine, $C_1$-$C_4$ amide or sulfamide or phosphoamide, imidazolidine-2,4-dilactone, other heterocyclic group, hydroxyl, or amino group. Exemplary lipophilic side chains or linkers have a cohesive energy density of about ≤20 $(J/cm^3)^{1/2}$ and relatively limited hydrogen bonding, as discussed for instance in D. W. Van Krevelen, *Properties of Polymers: Their Estimation and Correlation With Chemical Structure*, $2^{nd}$ Ed. (1976, Elsevier), pp. 129-159. In certain embodiments the side chain can be a linker.

cc) Stable

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

dd) Backbone Atom

The term backbone atom when used herein with respect to a linker refers to an atom in the shortest direct path of covalent bonding between the two chief moieties that are linked by the linker.

ee) Linker

The term linker as used herein refers to a bond or organic moiety that is covalently bonded to a fluorophore moiety and to a residue that can bind to an ion channel or enzyme. A linker may have C—C bonds directly to an aromatic or heteroaromatic ring that is being linked, or may be bonded to the ring through heteroatoms in a moiety such as an amide, sulfamide, or other group. In certain embodiments the linker can be a lipophilic side chain.

ff) Small Aromatic Ring System

The term small aromatic ring system as used herein refers to a mono-, bi-, or tricyclic aromatic ring system. The term aromatic as used herein refers to a carbocyclic structure having aromatically delocalized electrons.

gg) Small Heteroaromatic Ring System

The term small heteroaromatic ring system as used herein refers to a mono-, bi-, or tricyclic heteroaromatic ring system. The term heteroaromatic as used herein refers to a cyclic structure having at least one carbon and at least one heteroatom in a ring wherein the ring has aromatically delocalized electrons.

hh) Electron Donating Group

The term electron donating group (EDG) as used herein has its usual meaning in the art, and refers to a moiety having a relatively low electronegativity and thus a relatively strong tendency to donate electron density to less electron-rich moieties.

ii) Electron Withdrawing Group

The terms electron withdrawing group (EWG) and electron accepting group (EAG) as used herein are synonymous, have their usual meaning in the art, and refer to a moiety having a relatively high electronegativity and thus a relatively strong tendency to attract or receive electron density from more electron-rich moieties.

8. Coapplication

"Coapplication" is defined as the application of one or more substances simultaneously, such as in the same formulation or consecutively, within a time frame such that each substance is active during a point when the other substance or substances are active.

9. Comprise

Throughout the description and claims of this specification, the word "comprise" and variations of the word, such as "comprising" and "comprises," means "including but not limited to," and is not intended to exclude, for example, other additives, components, integers or steps.

10. Control

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

11. Enzyme Modulator

The term enzyme modulator as used herein refers to a molecule that can bind to an ion channel or enzyme, thereby modulating its activity, and includes both reversible and irreversible modulators.

12. Fluorescent

The term fluorescent as used herein can be defined as a molecule having luminescence that is caused by the absorption of radiation at one wavelength followed by nearly immediate reradiation usually at a different wavelength and that ceases almost at once when the incident radiation stops, as understood in the art.

13. Fluorophore Moiety

The term fluorophore moiety as used herein refers to a moiety that has fluorescent properties. Illustrative fluorophore moieties for the present invention include dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7; as well as additional examples such as 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

14. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

15. In vitro In vivo

The terms in vitro and in vivo as used herein have their usual and ordinary meanings in the art.

16. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

17. Label

The terms label and tag as used herein with reference to a fluorescent species are interchangeable and refer to its presence as a moiety covalently bound to another residue such as an antibody or a drug species, wherein the fluorescence of the label enables the location and or activity of the other residue to be monitored.

18. Modulate

The terms modulate, modulator and modulation as used herein refers to an effect that changes the rate or throughput of an enzyme or ion channel by 10% or more relative to its pre-modulation state.

19. Optionally

"Optional" or "optionally" means that the subsequently described event or circumstance may or may not occur, and that the description includes instances where said event or circumstance occurs and instances where it does not.

20. Passive

The term passive as used herein with reference to fluorescent species refers to their use for fluorescence as opposed to enhancement of binding affinity.

21. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

22. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

23. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

24. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

25. Reduce

By "reduce" or other forms of reduce means lowering of an event or characteristic. It is understood that this is typically in relation to some standard or expected value, in other words it is relative, but that it is not always necessary for the standard or relative value to be referred to.

For example, "reduces phosphorylation" means lowering the amount of phosphorylation that takes place relative to a standard or a control.

26. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

27. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

28. Tissue

Tissue or like terms refers to a collection of cells. Typically a tissue is obtained from a subject.

29. Treating

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertently cause harm.

30. Therapeutically Effective

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

B. Compositions and Methods

1. Compositions

Cyclin-dependent kinases (CDK) are classic Ser/Thr kinases with molecular weights of 30-40 kDa, play an important and well-defined role in cell cycle regulation and involved in signaling pathways required for several aspects of cell division and proliferation (Nigg E A. Curr Opin Cell Biol 1993; 5:187-193; Nigg E A. Bioessays 1995; 17:471-40; Senderowicz A M. Oncogene 2003; 22:6609-6620; Morgan D O. Annu Rev Cell Dev Biol 1997; 13:261-291). All CDK enzymatic activation requires the binding of a regulatory cyclin subunit. Thus, CDK-cyclin complexes are needed for phosphorylation of key proteins during cell cycle events (Chu X J, et al. J Med Chem 2006; 49:6549-6560.). Abnormal activation of various CDKs leading to deregulated cell cycle progression is a common feature in many cancers (Sherr C J. Science 1996; 274:1672-1677; Harper J W, Elledge S J. Curr Opin Genet Dev 1996; 6:56-64). Given these pivotal roles of CDKs in cancers, targeting CDKs is considered an intelligent strategy to block and/or interfere with tumor cell proliferation. (Shapiro G I. J Clin Oncol 2006; 24:1770-1783; Vermeulen K, et al. Cell Prolif 2003; 36:131-149; Collins I, Garrett M D. Curr Opin Pharmacol 2005; 5:366-373). Different classes of CDK inhibitors have been characterized including purine-based compounds, alakaloids, butyrolactone, flavonoids which are either currently in clinical trails or under development (Huwe A, et al. Angew Chem Int Ed Engl 2003; 42:2122-2138; Davies T G, et al. Nat Struct Biol 2002; 9:745-749; Chang Y T, et al. Chem Biol 1999; 6:361-375; Gray N S, et al. Science 1998; 281:533-538; Senderowicz A M, et al. J Natl Cancer Inst 2000; 92:376-387).

Despite differences in chemical structures, most of these CDK inhibitors employ competitive inhibition of ATP binding at the catalytic site as the principal mechanism of CDK inhibition, which has emerged as a relatively effective drug discovery strategy (Davies T G, et al. Pharmacol Ther 2002; 93:125-133; Knockaert M, et al. Trends Pharmacol Sci 2002; 23:417-425). However, specificity of CDK inhibitors is a major issue due to high degree of sequence similarity within the active site of CDKs and a large number of other protein kinases. Besides this specificity, selective targeting of present CDK inhibitors to intracellular targets and intratumoral distribution is not yet completely understood. Therefore, development of potent and selective CDK inhibitors that provide an imageable "readout" would be extremely useful.

Previous reports have shown that, introduction of dansyl group covalently into Estramustine (EM), a antineoplastic agents permitted visualization of EM into live cells in human prostate cancer cells (Stearns M E, et al. Proc Natl Acad Sci USA 1985; 82:8483-8487). Another report demonstrated that genetically encoded dansylalanine in Saccharomyces cerevisiase by using an amber nonsense codon and corresponding orthogonal tRNA/aminoacyl-tRNA synthetase pair could be used as an excellent tool to study the both biochemical and cellular studies of protein structure and function (Summerer D, et al. Proc Natl Acad Sci USA 2006; 103:9785-9789.). A recent report studied the early stage of death process using small non-peptidic fluorescent compound N,N'-Didansyl-L-cysteine called Aposense which were selective targeted within the apoptotic and necrotic cell cytoplasm (Damianovich et al. Eur J Nucl Med Mol Imaging 2006; 33:281-291;

Cohen A et al. Technol Cancer Res Treat 2007; 6:221-234). By taking advantage of the inherent fluorescence of dansyl group, purvanalol B was chemically modified to yield two fluorescent derivatives of purvanalol B namely VMY-1-101 and VMY-1-103. By taking advantage of inherent fluorescence property of the dansyl group and its importance in identification of intracellular targets, a method was developed to design and synthesize fluorescently tagged dansylethylenediamine variants of most specific and potent CDK inhibitors. Using structure based design, low molecular weight fluorophore (dansyl ethylenediamine) were covalently bond to Purvalanol B (a known CDK inhibitor) at specific positions without diminishing CDK activity. These new compounds (designated as VMY-1-101 and VMY-1-103) with fluorescent properties, enables simultaneous assess to their intracellular localization as well as their CDK inhibitory activities by biochemical means. The cellular effects of novel compounds were studied in relation to inhibition of cell proliferation and cell cycle progression and ability to potentiate the apoptotic response in two human adenocarcinoma cells, p53-mutated and estrogen independent MDA-MB-231 cells and wild type p53 and estrogen dependent MCF-7 cells and compared these compounds with other known CDK inhibitors, such as, purvalanol B and Roscovitine. The new compounds demonstrated improved cellular toxicity against human breast cancer cell lines as compared to Purvalanol B, induced enhanced cell cycle arrest at G2/M phase in human breast cancer cells. Besides cell cycle arrest, these compounds also induce apoptosis as demonstrated by down regulation of anti-apoptotic and up-regulation of pro-apoptotic proteins, PARP cleavage analysis and Annexin-V binding assay. Biochemically, phospho-CDC2 expression level was inhibited implying a potential decrease of CDC2 kinase activity which is required for either G2/M entry or mitotic progression, which further corroborates the compounds' ability to induce a effective G2/M check point and cell cycle arrest. Confocal images confirm the intracellular delivery and localization of VMY-1-103 in the cytoplasm of the human breast cancer cells. In summary, a strategy to design and synthesize a class of fluorescent CDK inhibitors and its potent irreversible anti-proliferative effect and pro-apoptotic effects are demonstrated and finally these CDK analogs were imaged in human breast cancer cells and provide a platform for future preclinical studies.

Disclosed are compositions, comprising a CDK inhibitor and a fluorescent moiety. The CDK inhibitor can be roscovitine or a derivative thereof. The CDK inhibitor can be purvalanol B or a derivative thereof. The CDK inhibitor can be purvalanol A or a derivative thereof. The CDK inhibitor can be flavopiridol or a derivative thereof. The CDK inhibitor can be staurosporine or a derivative thereof. The fluorescent moiety can be any fluorescent moiety describe elsewhere herein. The fluorescent moiety can be a dansyl moiety or a derivative thereof.

Disclosed are compositions comprising a roscovitine analog or a purvalanol analog, wherein the analog comprises at the $N_9$ position of the purine a $C_{1-4}$ alkyl group; at the $C_6$ of the purine a small amino substituted aromatic or small heteroaromatic ring system, further substituted with a moiety consisting of carboxylic acid, amide, sulfamide and phosphamide attached to a linker, wherein the linker is a attached to a fluorophore moiety.

Also disclosed are compositions, wherein the linker is a lipophilic side chain, further comprising a substituted hydrocarbon amine at the purine $C_2$ position, wherein the $C_{1-4}$ alkyl group is iso-propyl, wherein the ring system comprises 4-amino-2-chloro-benzoic acid, 4-amino-benzoic acid, 4-aminomethyl-benzoic acid, or 4-aminomethyl-2-chloro-benzoic acid, wherein the substituted hydrocarbon amine at the purine $C_2$ position has (R) stereochemistry, wherein the substituted hydrocarbon amine at the purine $C_2$ position has (L) stereochemistry, wherein the substituted hydrocarbon amine at the purine $C_2$ position is racemic, wherein the substituted hydrocarbon amine comprises 2-amino-1-butanol or 2-amino-3-methyl-1-butanol, wherein the amino butanol is (R)-2-amino-1-butanol or (R)-(–)-2-amino-3-methyl-1-butanol, wherein the linker has 8 backbone atoms or less, wherein the fluorophore moiety comprises a side chain comprising dansyl ethylenediamine and/or alone or in any combination with these or any other characteristic disclosed herein.

Disclosed are compositions comprising a roscovitine analog or a purvalanol analog, wherein the analog comprises at the $N_9$ position of the purine a $C_{1-4}$ alkyl group; at the $C_6$ of the purine a small amino substituted aromatic or small heteroaromatic ring system, further substituted with a moiety consisting of carboxylic acid, amide, sulfamide and phosphamide attached to a reactive moiety.

Also disclosed are compositions, further comprising a substituted hydrocarbon amine at the purine $C_2$ position, wherein the $C_{1-4}$ alkyl group is iso-propyl, wherein the ring system comprises 4-amino-2-chloro-benzoic acid, 4-amino-benzoic acid, 4-aminomethyl-benzoic acid, or 4-aminomethyl-2-chloro-benzoic acid, wherein the substituted hydrocarbon amine at the purine $C_2$ position has (R) stereochemistry, wherein the substituted hydrocarbon amine at the purine $C_2$ position has (L) stereochemistry, wherein the substituted hydrocarbon amine at the purine $C_2$ position is racemic, and/or alone or in any combination with these or any other characteristic disclosed herein.

Disclosed are compositions, wherein the substituted hydrocarbon amine comprises 2-amino-1-butanol or 2-amino-3-methyl-1-butanol, wherein the amino butanol is (R)-2-amino-1-butanol or (R)-(–)-2-amino-3-methyl-1-butanol, wherein the linker has 8 backbone atoms or less, wherein the fluorophore moiety comprises a side chain comprising dansyl ethylenediamine, wherein the reactive moiety comprises an acid or a nuclephile, wherein the reactive moiety is an optionally substituted $C_{1-4}$ amino group, and/or alone or in any combination with these or any other characteristic disclosed herein.

Also disclosed are compositions, wherein the fluorophore moiety comprises dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7; 3-hydroxypyrene 5,8,10-trisulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC, and/or alone or in any combination with these or any other characteristic disclosed herein.

Disclosed are compositions, wherein the fluorophore moiety comprises dansyl or a fluorophore moiety of the same or lower molecular weight, wherein the fluorophore moiety comprises dansyl, wherein the reactive moiety is a halide, halogenated conjugate base of an acid, tosylate, or pyridinium bonded to an acid moiety, wherein the acid moiety bonded to the leaving group is —CO$_2$H, —SO$_3$H, —SO$_2$H, —PO$_3$H, PO$_2$H, or B(OH)$_2$, wherein the acid moiety can be selectively activated by reaction with EDCI and N,O-dimethylhydroxylamine HCl, wherein the selectively activated acid moiety is a Weinreb amide, wherein the anion of a small aryl group or small heteroaryl group is provided as a Grignard reagent or a lithiated aryl or heteroaryl group and/or alone or in any combination with these or any other characteristic disclosed herein.

2. Methods

Disclosed are methods of labeling a cell, comprising incubating a fluorescence labeled molecule, wherein the fluorescence labeled molecule specifically interacts with a protein present on or in the cell, wherein the incubating occurs in conditions allowing interaction of fluorescence labeled molecule with the protein.

Disclosed are methods of detecting a tumor cell comprising incubating a potential tumor cell with a compound, wherein the compound interacts with a protein on a tumor cell, where the presence or absence of the protein on the tumor indicates is related to a tumor cell, wherein the compound comprises a fluorescent moiety, identifying the association of fluorescence with the potential tumor cell.

Also disclosed are methods of treating and detecting a tumor cell comprising incubating a potential tumor cell with a compound, wherein the compound interacts with a protein on a tumor cell, wherein the presence or absence of the protein on the tumor indicates it is related to a tumor cell, wherein the presence of the compound with the cell indicates the protein is present, wherein the compound comprises a fluorescent moiety, identifying the association of fluorescence with the potential tumor cell. Also disclosed are methods, wherein the compound inhibits tumor cell growth.

Also disclosed are methods, comparing the fluorescence of the potential tumor cell to a control.

Also disclosed are methods, wherein the compound comprises any compound disclosed herein.

Also disclosed are methods, wherein the detection occurs in vivo.

Also disclosed are methods, wherein the detection occurs in situ.

Also disclosed are methods, wherein the potential tumor cell is a potential prostate tumor.

Disclosed are methods for synthesizing roscovitine and purvalanol analogs, comprising the steps of: a) providing 2-fluoro-6-chloro-purine; b) functionalizing the N$_9$ position of the purine with a C$_{1-4}$ alkyl group; c) providing a small aromatic or small heteroaromatic ring system that is substituted with an amino group and with a protected or unprotected group selected from the moieties consisting of carboxylic acid, amide, sulfamide and phosphamide; d) adding the amine group of the small aromatic or small heteroaromatic ring system to the purine C$_6$ position; e) condensing the protected or unprotected group with a linker that is a side chain on a fluorophore moiety; and f) adding an optionally substituted hydrocarbon amine at the purine C$_2$ position.

Also disclosed are methods, wherein the C$_{1-4}$ alkyl group is iso-propyl, wherein the iso-propyl group is added by reaction of 2-fluoro-6-chloro-purine with iso-propyl alcohol, DEAD, and triphenyl phosphine, wherein the amine group is added in the presence of DIEA, wherein the ring system is provided in the form of 4-amino-2-chloro-benzoic acid, 4-amino-benzoic acid, 4-aminomethyl-benzoic acid, or 4-aminomethyl-2-chloro-benzoic acid, wherein addition at the purine C$_2$ position is performed in the presence of DIEA, wherein addition at the purine C$_2$ position is performed with chiral or racemic 2-amino-1-butanol or 2-amino-3-methyl-1-butanol, wherein the amino butanol is (R)-2-amino-1-butanol or (R)-(−)-2-amino-3-methyl-1-butanol, wherein the linker has 8 backbone atoms or less, wherein the fluorophore moiety comprises a side chain comprising dansyl ethylenediamine, and/or alone or in any combination with these or any other characteristic disclosed herein.

Disclosed are methods for synthesizing roscovitine and purvalanol analogs, comprising the steps of: a) providing 2-fluoro-6-chloro-purine; b) functionalizing the N$_9$ position of the purine with a C$_{1-4}$ alkyl group; c) providing a small aromatic or small heteroaromatic ring system that is substituted with an amino group and with a protected or unprotected group selected from the moieties consisting of carboxylic acid, amide, sulfamide and phosphamide; d) adding the amine group of the small aromatic or small heteroaromatic ring system to the purine C$_6$ position; e) optionally condensing the protected or unprotected group with a reactive moiety, f) adding an optionally substituted hydrocarbon amine at the purine C$_2$ position.

Also disclosed are methods, wherein the C$_{1-4}$ alkyl group is iso-propyl, wherein the iso-propyl group is added by reaction of 2-fluoro-6-chloro-purine with iso-propyl alcohol, DEAD, and triphenyl phosphine, wherein the amine group is added in the presence of DIEA, wherein the ring system is provided in the form of 4-amino-2-chloro-benzoic acid, 4-amino-benzoic acid, 4-aminomethyl-benzoic acid, or 4-aminomethyl-2- chloro-benzoic acid, wherein addition at the purine $C_2$ position is performed in the presence of DIEA, wherein addition at the purine $C_2$ position is performed with chiral or racemic 2-amino-1-butanol or 2-amino-3-methyl-1-butanol, wherein the amino butanol is (R)-2-amino-1-butanol or (R)-(−)-2-amino-3-methyl-1-butanol, wherein the reactive moiety is an acid or a nuclephile, wherein the reactive moiety is an optionally substituted $C_{1-4}$ amino group, and/or alone or in any combination with these or any other characteristic disclosed herein.

Also disclosed are compositions, wherein the fluorophore moiety is dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7; 3-hydroxypyrene 5,8,10-trisulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC, wherein the fluorophore moiety is dansyl or a fluorophore moiety of the same or lower molecular weight wherein the fluorophore moiety is dansyl, and/or alone or in any combination with these or any other characteristic disclosed herein.

Disclosed are methods of labeling a cell, comprising incubating a fluorescence labeled molecule, wherein the fluorescence labeled molecule specifically interacts with a protein present on or in the cell, wherein the incubating occurs in conditions allowing interaction of fluorescence labeled molecule with the protein.

Disclosed are methods of detecting a tumor cell comprising incubating a potential tumor cell with a compound, wherein the compound interacts with a protein on a tumor cell, where the presence or absence of the protein on the cell indicates it is related to a tumor cell, wherein the compound comprises a fluorescent moiety, identifying the association of fluorescence with the potential tumor cell.

Also disclosed are methods, comparing the fluorescence of the potential tumor cell to a control.

Disclosed are compositions produced by any of the method disclosed herein and/or alone or in any combination with these or any other characteristic disclosed herein.

Disclosed are methods, wherein the detection occurs in vivo or in situ and/or alone or in any combination with these or any other characteristic disclosed herein.

Also disclosed are methods, wherein the potential tumor cell is a potential prostate tumor, and/or alone or in any combination with these or any other characteristic disclosed herein.

A method of labeling a cell, comprising incubating a fluorescence labeled molecule, wherein the fluorescence labeled molecule specifically interacts with a protein present on or in the cell, wherein the incubating occurs in conditions allowing interaction of fluorescence labeled molecule with the protein.

A method of detecting a tumor cell comprising incubating a potential tumor cell with a compound, wherein the compound interacts with a protein on a tumor cell, where the presence or absence of the protein on the cell indicates it is related to a tumor cell, wherein the compound comprises a fluorescent moiety, identifying the association of fluorescence with the potential tumor cell.

3. Inhibitor Identification and Optimization

Examples of suitable fluorophore moieties for use in the invention include but are not limited to the following: dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Additional suitable specific examples include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethaneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

4. Exemplary Inhibitor Molecules and Their Syntheses a) Roscovitine Family

Roscovitine, also known as seliciclib, is 2-(R)-(1-ethyl-2-hydroxyethylamino)-6-benzylamino-9-isopropylpurine, shown at SCHEMEs disclosed herein. It is known to inhibit cyclin-dependent kinases (CDKs).

5. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue. (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue. (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed. (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder is effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody, for treating, inhibiting, or preventing a cancer, such as prostate cancer, the efficacy of the therapeutic antibody can be assessed in various ways well known to the skilled practitioner The compositions that inhibit disclosed human Na channel and cancer, such as prostate cancer, interactions disclosed herein may be administered as a therapy or prophylactically to patients or subjects who are at risk for the cancer or prostate cancer.

6. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

7. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed herein, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, disclosed human Na channels, are also disclosed. Thus, the products produced using the combinatorial or screening approaches that involve the disclosed compositions, such as, disclosed human Na channels, are also considered herein disclosed.

It is understood that the disclosed methods for identifying molecules that inhibit the interactions between, for example, disclosed human Na channel can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).[113]

As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, disclosed human Na channel, are also disclosed. Thus, the products produced using the molecular modeling approaches that involve the disclosed compositions, such as, disclosed human Na channels, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090.[1] Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

8. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring prostate cancer, comprising one or more of the molecules disclosed herein.

C. Methods of Making the Compositions

The compositions disclosed herein and the compositions necessary to perform the disclosed methods can be made using any method known to those of skill in the art for that particular reagent or compound unless otherwise specifically noted.

1. Process Claims for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

D. Methods of Using the Compositions

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 Design and Synthesis of Fluorescent CDK Analogs

A new class of molecules, Roscovitine and Purvalanol-B based analogs, have been designed and synthesized to act as a cyclin-dependent kinase (CDK) inhibitors for cancer treatment, diagnostics, and to further improve the knowledge about CDK activity in relations to diseases, including cancer. The inhibitor has a fluorescent moiety that can serve at least two wanted properties (1)—the fluorescence can be used as a tracking device to further understand and study the intermolecular localization of the drug. It can also serve as a confirmation platform in which it can be visually confirmed that the drug has successfully entered and targeted the wanted cells. (2)—the fluorescent tag can also increase the inhibition of the drug towards the targeted cells making the drug more effective. This strategy, as discussed, could give more successful and well understood outcome of the drug performance and mechanism. The structures of the present fluorescent compounds are shown below

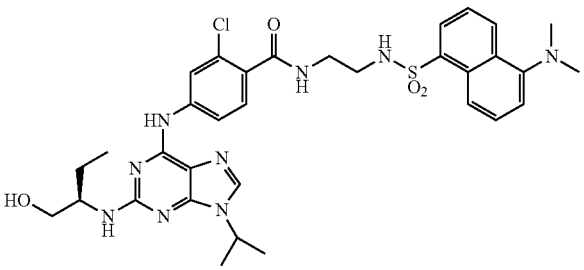

VMY-1-101

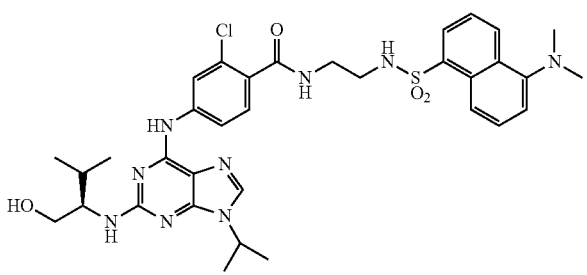

VMY-1-103

2. Example 2: Disclosed Compounds and Methods

Disclosed herein is a molecular class which relates to the treatment of diseases associated with cyclin-dependent kinases (CDK), including cancer and inflammation. Typically diseases involving CDK is a result of a hyperactive CDK resulting in unrestrained cell proliferation, a hallmark of cancer. CDK inhibitors, such as Roscovitine and Purvalanol (A and B), have previously been developed as potential treatments for discussed CDK activity and therefore diseases. Here, a fluorescent moiety (dansyl) was synthetically incorporated into the already known potent CDK inhibitor Purvalanol-B. The dansyl group was strategically placed so the performance of the drug was not only preserved but also enhanced. The increase in hydrogen bonding due to the linker between the phenylchloride and the dansyl group can lead to the enhancement of CDK inhibition of the Purvalanol-B analog compared to Purvalanol-B, See FIG. 3 The carboxylic acid group on Purvalanol-B was used for further functionalization to form an amide linker on the phenylchloride of Purvalanol-B (Scheme 1). The new fluorescent Purvalanol analog is shown to have a higher inhibition affinity toward human breast cancer lines (MDA-MB-231 and MCF7) then Pruvalanol-B itself. Also, the fluorescent dansyl group provides a source for imaging where/if the drug present in the targeted cells which can be useful for both understanding the mechanism of the drug but also a source of confirmation that the drug actually has been delivered to its target. This provides information related to advancements in treatments associated with hyperactive CDKs. Development of potent, selective and fluorescent CDK inhibitors would provide "trackable" compounds useful for detailed in vivo and in vitro study of molecular pathways responsible for CDK activation. To achieve these aims, fluorescently tagged variants of some of the most specific and potent CDK inhibitors were designed and synthesized. These compounds provide an opportunity to assess their in vivo ability to reach desired molecular targets, and to study their intracellular localization. A strategy for the selective and efficient synthetic incorporation of low-molecular-weight fluorophores into Roscovitine and Purvalanol B (CDK inhibitors) at specific positions that do not diminish their cellular CDK activity is disclosed herein.

different methods (Method 1: 2% to 60% B in A over 20 min, Method 2: 50% to 60% B in A over 20 min), Restek's Ultra IBD 5 μμm column (4.6 mm×50 mm) and a flow rate of 1 mL/min Scheme 1: Synthesis of VMY-1-101 and VMY-1-103.

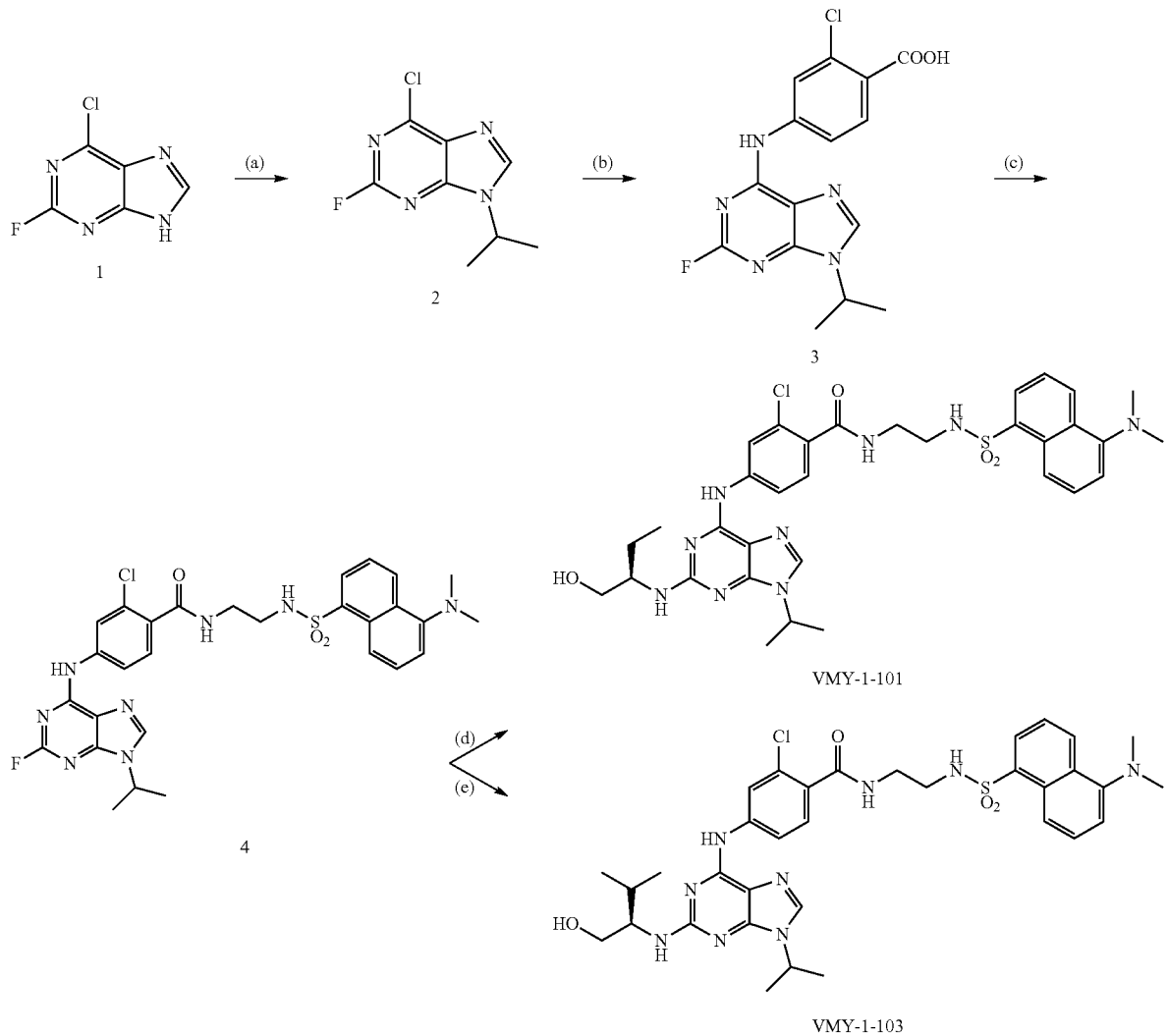

Reagents and conditions: (a) iPrOH, DEAD, PPh$_3$, THF -10° C.-RT (b) 4-Amino-2-chloro-benzoic acid, DIEA, n-butanol, 140° C.
(c) Dansyl ethylenediamine, DIEA, EDCl, HOBt, DMF:CH$_2$Cl$_2$:Dioxane (1:1:1) (d) R-2-amino-1-butanol (excess), DIEA, 140° C.
(e) (R)-(-)-2-amino-3-methyl-1-butanol, DIEA, n-butanol, 110° C., 48 hours 3. Example 3: Synthetic Procedure for fluorescent CDK Inhibitors a) General Methods All reagents and solvents were commercially available and used without further purification. Flash chromatography was performed for purification of compounds. NMR spectra were recorded using $^1$H (400 MHz) and $^{13}$C (100 MHz). Chemical shifts (δ) are given in ppm downfield from tetramethylsilane, as internal standard, and coupling constants (J-values) are in hertz (Hz). Purity of final compounds were found to be more than 95% pure by reversed phase HPLC analysis (Shimadzu Model LC 2010) using A: Water, B: Acetonitrile with two b) 2-Fluoro-6-chloro-9-isopropylpurine (2)

Anhydrous tetrahydrofuran (60 mL) is added to a flame-dried flask under N$_2$ containing 2-fluoro-6-chloropurine (1.8 g, 10.4 mmol) and triphenylphosphine (6 g, 20.8 mmol). To this anhydrous 2-propanol (1.6 ml, 20.8 mmol) is added, and the mixture is then cooled to −10° C. After dropwise addition of 40% (W/V) diethyl azodicarboxylate in tetrahydrofuran (9 ml, 20.8 mmol), the mixture is warmed gradually to room temperature. After 18 h, the reaction mixture is quenched with 1 ml of water and the solvent is removed in vacuo. The resulting yellow oil is purified by column chromatography. The resulting solid is triturated with methanol (to remove the diethyl hydrazine-N,N'-dicarboxylate ester by-products) to yield 1.1 g (49%) as a white solid.

c) 2-Fluoro-6-(3-chloro-4-carboxyanilno)-9-isopropylpurine (3)

4-Amino-2-chlorobenzoicacid (0.32 g, 1.863 mmol), 2-Fluoro-6-chloro-9-isopropylpurine (0.4 gm, 1.863 mmol), and diisopropylethylamine (0.8 mL, 2.5 mmol) are combined in n-butanol in a sealed tube and heated for 12 hours at 80° C. After removal of the solvents in vacuo, the crude product is resuspended in $CH_2Cl_2$, collected by filtration, and washed with cold 50 mM HCl, $CH_2Cl_2$, and ether to yield 675 mg (III) as a white solid. The crude product was used further reaction without purification. $^1$H NMR (400 MHz, $CDCl_3$): 1.65 (d, 6H). 4.85 (m, 1H), 8.16 (s, 1H)

d) 2-Chloro-N-[2-(5-dimethylamino-naphthalene-1-sulfonylamino)-ethyl]-4-(2-fluoro-9-isopropyl-9H-purin-6-ylamino)-benzamide (4)

To a mixture of $CH_2Cl_2$, Dioxane, DMF (1:1:1, 30 mL) containing compound III (0.67 g, 1.934 mmol) and dansyl ethylenediamine (0.736 g, 2.514 mmol) were added diisopropylethylamine (0.70 mL, 4.06 mmol) and HOBT hydrate (0.33 g, 2.514 mmol) followed by EDC (0.48 g, 2.514 mmol). The mixture was stirred for 24 hours and then concentrated. The residue was dissolved in chloroform (100 mL) and taken into a separator funnel. The organic layer was washed with 100 mL portion of 10% citric acid, saturated Licl and brine. The organic layer was separated, dried with anhydrous sodium sulfate, filtered and concentrated under reduced pressure to give crude product which was purified by column chromatography as a yellow solid (0.52 g, 44%). ESI (m/z) 625. 1724 $M^++1$ for $C_{29}H_{30}ClFN_8O_3S$. $^1$H NMR (400 MHz, DMSO-$d_6$): δ 1.51 (d, 6H), 4.69 (m 1H), 7.83 (d, 1H, J=8.7 Hz), 7.93 (dd, 1H, J=2.1 Hz, J=8.7 Hz), 8.16 (s, 1H), 10.74 (s, 1H)

e) 2-Chloro-N-[2-(5-dimethylamino-naphthalene-1-sulfonylamino)-ethyl]-4-[2-(1-hydroxymethyl-propylamino)-9-isopropyl-9H-purin-6-ylamino]-benzamide (VMY-1-101)

A mixture of Compound (IV) (0.1 g, 0.16 mmol), excess of R-(-)-2-amino-1-butanol (5 mL,), and diisopropylethylamine (0.2 mL, 1.217 mmol) in a sealed tube and heated at 120° C. for 48 hours. After cooling to room temperature, the combined organic layers were diluted with chloroform, extracted with water and brine, the organic layer was separated and dried over anhydrous sodium sulfate, filtered and concentrated under reduced pressure to give crude product which was purified by flash chromatography as a gummy solid (0.07 g, 63%). ESI (m/z) 694.2437 $M^++1$ for $C_{33}H_{40}ClN_9O_4S$. $^1$HNMR (400 MHz, $CDCl_3$): δ 1.58 (d, 6H, J=6.7 Hz), 2.83 (s, 6H), 3.18 (dd, 2H, J=5.7 Hz, J=10.8 Hz), 3.49 (m, 2H), 4.75 (m, 1H), 6.95 (s, 2H, J=5.6 Hz), 7.08 (d, 1H. J=7.6 Hz), 7.34 (m, 2H), 7.47 (t, 1H, J=7.9 Hz), 7.56 (dd, 1H, J=1.5 Hz, J=8.6 Hz), 7.87 (s, 1H), 7.94 (s, 1H), 8.25 (m, 2H), 8.49 (d, 1H, J=8.6 Hz), 8.65 (s, 1H), $^{13}$C (100 MHz, $CDCl_3$); δ 166.870, 157.106, 152.764, 152.563, 151.908, 150.975, 150.787, 140.898, 139.354, 134.454, 131.226, 130.545, 129.783, 129.478, 129.402, 128.594, 128.349, 123.108, 120.866, 118.156, 115.178, 47.698, 45.326, 42.816, 39.8040, 22.449. See FIG. 19 for HPLC condition and results.

f) 2-Chloro-N-[2-(5-dimethylamino-naphthalene-1-sulfonylamino)-ethyl]-4-[2-(1-hydroxymethyl-2-methyl-propylamino)-9-isopropyl-9H-purin-6-ylamino]-benzamide (2)VMY-1-103

Compound III (0.15 g, 0.24 mmol), R-(-)-2-amino-3-methyl-1 butanol (0.12 g, 1.21 mmol), and diisopropylethylamine (0.2 mL, 1.217 mmol) are dissolved in n-butanol in a sealed tube and heated at 120° C. for 24 hours. After 24 hours add 0.38 mmol R-(-)-2-amino-3-methyl-1-butanol and 0.2 ml of diisopropylethylamine and continued for 48 hours. After removal of the solvent in vacuo, the crude product is resuspended in $CH_2Cl_2$ and washed with water followed by brine, the organic layer was separated and dried over anhydrous sodium sulfate, filtered and concentrated under reduced pressure to give crude product which was purified by column chromatography as a gummy solid (0.07 g, 63%). ESI (m/z) 708.2659 $M^++1$ for $C_{34}H_{42}ClN_9O_4S$. $^1$H NMR (400 MHz, $CDCl_3$): δ 0.98 (t, 3H, J=7.4 Hz), 1.44 (dd, 6H, J=5.7 Hz, J=20.9 Hz), 1.62 (m, 2H), 2.84 (s, 6H), 3.18 (s, 2H), 3.49 (tt, 2H, J=7.1 Hz, J=19.7 Hz), 3.65, (m, 1H), 3.91-4.03 (m, 2H), 4.47 (s, 1H), 5.43 (d, 2H, J=86.8 Hz), 7.10 (dd, 2H, J=2.7 Hz, J=7.9 Hz), 7.45 (m, 4H), 7.57 (s, 1H), 8.23 (dd, 1H, J=1.1 Hz, J=7.3 Hz), 8.34 (d, 1H, J=8.6 Hz), 8.50-8.55 (m, 1H). $^{13}$C (100 Mhz, $CDCl_3$) δ 167.133, 159.192, 151.851, 151.060, 135.362, 134.851, 130.863, 130.808, 130.379, 129.836, 129.789, 129.498, 129.347, 129.248, 128.248, 127.185, 123.140, 120.027, 118.827, 117.152, 117.168, 115.142, 114.487, 55.532, 45.360, 42.735, 40.277, 22.532, 22.333, 10.804. See FIG. 19 for HPLC conditions and results.

4. Example 4: Kinase Assay

Compounds VMY-1-101 and VMY-1-103 were tested in comparison to Roscovitine and Purvalanol B for inhibition of various CDKs (CDK1/B, CDK2/A, CDK2/E, CDK3/E, CDK7/cyclinH/MAT1). 100 nM solutions were prepared of the mentioned compounds and drugs. The final reaction was carried out in a 25 μL solution. The respective kinases (at 5-10 mM were incubated with 8 mM MOPS (pH 7.0), 0.2 mM EDTA, 0.1 mg/ml histone H1, 10 mM MgAcetate and [γ-33P-ATP] (specific activity approximately 500 cpm/pmol, concentration as required). The reaction was then initiated by the addition of the MgATP mix. The reaction was stopped after 40 min of incubation by adding 5 μL of a 3% phosphoric acid solution. 10 μL of the reaction was spotted onto a P30 filter mat and washed 3 times for 5 min in 75 mM phosphoric acid and one in methanol prior to drying and counted radioactivity by scintillation counting. Compounds VMY-1-101 and VMY-1-103 VMY-1-101 consistently out performed Roscovitine in % inhibition. The compounds had comparable results to Purvalanol B. Compounds VMY-1-101 and VMY-1-103 VMY-1-101 had 87% and 89% selective inhibition for CDK2/E compared to other CDK/cyclin complexes, see Table 1. Table 1 summarizes the cytotoxic effects of VMY compounds and its controls on breast cancer cell line.

The added fluorescent moiety provides a "tracking" system for the drug during treatment and here it is shown that the incorporation of the dansyl group does not significantly influence the inhibition performance compared to the parent drug (Purvalanol-B)

TABLE 1

| Protein Kinase | VMY-1-101 (0.1 μM) | VMY-1-103 (0.1 μM) | Roscovitine (0.1 μM) | Purvalanol (0.1 μM) |
| --- | --- | --- | --- | --- |
| CDK1/cyclinB | 16 ± 3 | 35 ± 1 | 10 ± 5 | 78 ± 6 |
| CDK1/cyclinA | 62 ± 0 | 72 ± 1 | 41 ± 4 | 96 ± 0 |

TABLE 1-continued

| Protein Kinase | VMY-1-101 (0.1 µM) | VMY-1-103 (0.1 µM) | Roscovitine (0.1 µM) | Purvalanol (0.1 µM) |
|---|---|---|---|---|
| CDK2/cyclinE | 87 ± 0 | 89 ± 1 | 57 ± 4 | 98 ± 0 |
| CDK3/cyclinE | 40 ± 3 | 65 ± 3 | 20 ± 3 | 89 ± 0 |
| CDK7/cyclinH/MAT1 | 57 ± 0 | 69 ± 2 | 26 ± 5 | 66 ± 1 |

5. Example 5: Cytotoxic Studies

In vitro studies were performed on human breast cancer cells MDA-MB-231 and MCF-7 using Compounds VMY-1-101 and VMY-1-103 VMY-1-101 in comparison to Roscovitine and Purvalanol-A and B. 1 µM, 10 µM, 25 µM, 50 µM, and 100 µM concentrations were used for all compounds to determine the concentration in which the drugs achieve $IC_{50}$ (concentration yielding 50% growth inhibition), towards the mentioned breast cancer cells in a WST-1 assay. Compounds VMY-1-101 and VMY-1-103 VMY-1-101 need significantly lower concentration to achieve $IC_{50}$, See Table 2. Table 2 provides the inhibition of kinase activity in the presence of 100 nM of VMY compounds. This data further supports with the morphological changes of the treated cells as shown in FIG. 4.

TABLE 2

| Compound | MDA-MB-231 | MCF-7 |
|---|---|---|
| VMY-1-101 | 4.86 ± 1.24 | 19.05 ± 1.14 |
| VMY-1-103 | 4.06 ± 1.32 | 10.03 ± 1.25 |
| Roscovitine | 54.86 ± 1.27 | 55.01 ± 1.1 |
| Purvalanol-B | >100 | >100 |
| Dansyl ethylenediamine | >100 | >100 |

6. Example 6: Cell Cycle Analysis

The effect on cell cycle inhibition was studied in human breast cancer cells, MDA-MB-231 and MCF-7. 5 µM concentrations were used for all drugs tested. The cells were exposed to the vehicle (DMSO) or 5, 10 µM of the CDK inhibitors for 24 hrs. The cell cycle distribution was then assessed using standard procedures. It was shown that both Compounds VMY-1-101 and VMY-1-103 induced the cell cycle progression in G2/M phase irrespective of the breast cancer line. (FIG. 5 and Table 3). Table 3 provides the sub-G1 population (Indicates the apoptotic population) in cell cycle after exposed with VMY compounds.

TABLE 3

| | MDA-MB-231 | | | MCF-7 | | |
|---|---|---|---|---|---|---|
| Compound | % Sub-G1 | % G1 | % S | % Sub-G1 | % G1 | % S |
| Control | 1.15 ± 0.14 | 59.15 ± 1.03 | 29.20 ± 0.59 | 0.61 ± 0.03 | 63.70 ± 0.18 | 23.50 ± 0.56 |
| VMY-1-101 | 2.01 ± 0.19 | 51.5 ± 0.50 | 25.05 ± 0.45 | 2.08 ± 0.19 | 63.56 ± 1.20 | 10.75 ± 0.88 |
| VMY-1-103 | 2.17 ± 0.18 | 51.87 ± 0.80 | 25.15 ± 0.53 | 2.09 ± 0.08 | 61.02 ± 0.28 | 16.26 ± 0.24 |
| Purvalanol B | 1.19 ± 0.01 | 58.69 ± 0.54 | 29.86 ± 0.70 | 1.10 ± 0.03 | 64.37 ± 0.57 | 20.54 ± 0.57 |
| Roscovitine | 1.22 ± 0.06 | 57.59 ± 0.44 | 26.29 ± 0.32 | 0.73 ± 0.02 | 63.83 ± 0.58 | 19.88 ± 0.74 |

7. Example 7: Anti proliferative effect of VMY-1-103 is Irreversible

In order to examine whether the mechanism of anti proliferative effect of the present fluorescent compounds is Irreversible/Reversible, the MDA-MB-231 cells were exposed with 5 µM and 10 µM of VMY-1-103 and Roscovitine for 24 hours or medium was changed and cells were post-incubated in a drug free medium for further 48 h (24 h/MC/48). The cell cycle distribution was then analyzed by flow cytometry. As shown in the FIG. 6, VMY-1-103 induced cell cycle arrest at G2/M phase for 24 h and remained the same in G2/M phase after post incubation. In contrast, roscovitine induces the G2/M phase arrest at 24 h and went back to the normal stage after post incubation. These results further supported that the VMY-1-103 compound underwent a potent irreversible anti proliferative mechanism, compared to roscovitine.

8. Example 8: The Effect of VMY-1-103 on Multidrug Resistant Cell Lines

The effect of VMY-1-103 on multidrug resistant cell lines was studied and compared with paclitaxel. Table 4 represents the IC50 of the compounds in the individual cell lines along with the ratio of the difference. Table 4 summarizes the effect of VMY compounds in multidrug resistance cell line. In contrast to paclitaxel, VMY-103 had a comparable activity in both cell lines, MCF7 and CL 10.3, and the activity did not seem to be modulated by MDR.

TABLE 4

| | | $IC_{50}$, 72 HOURS | |
|---|---|---|---|
| Cell line | Origin | VMY-1-103 | Paclitaxel |
| MCF-7 | Breast | 4.5 mM | 2 nM |
| CL 10.3 | Breast (MDR) | 44.3 mM | 47.5 µM |
| CL 10.3 $IC_{50}$/MCF-7 $IC_{50}$ | | 9.8 | 2375 |

9. Example 9: Antiproliferative Mechanism of Fluorescent Compounds

As of now Purvalanol B is most potent purine based CDK inhibitor as per cell free kinase assay. Surprisingly, in our study, purvalanol B was showing insignificant cellular activity in breast cancer cells. The response of cell cycle protein level with purvalanol B and VMY-1-103 were identified. In order to address this issue the MDA-MB-231 cells were treated with purvalanol B and VMY-1-103 at 10 µM with different time intervals and compared for expression cell cycle proteins responsible for G2/M phase by immunoblotting. The expression levels principal component proteins, such as, phospho-Cdc2, Cdc2 and cyclin B were specific assessed. As shown in FIG. 7, after 6 h post-treatment, the VMY-1-103 treated cells resulted in a time-dependent decrease in expression of phospho-Cdc2 at both catalytic (T 161) and regulatory side (Y15) compare to control, where as purvalanol B, had no affect on the phospho-Cdc2 expression throughout the time period tested. The inhibition of the expression level of phospho-CDC2 in MDA-MB-231, further supports that VMY-1-103 decreases the CDC2 (CDK1) kinase activity, which halts cell division at G2/M check point. Membrane impermeability of purvalanol B attributed to its non and insignificant effect on Cdc2 activation may have occurred. Quantitative analysis of these bands showed a significant difference between VMY-1-103 and purvalanol B in terms of phospho expression levels of Cdc2.

10. Example 10: Intracellular Localization of VMY-1-103 and Binding Ability of VMY-1-103 on Human Breast Tissue It has already known that, CDK1/CyclinB kinase activation which is responsible for driving G2/M phase of the cell cycle occurs in cytoplasm as the cells progress into metaphase. Taking advantage of inherent fluorescent property of VMY-1-103 and examine the intracellular localization of VMY-1-103 in breast cancer cells. The cells were treated with 10 μM of VMY-1-103 for 1 h followed by fixation and visualization of cells by confocal microscopy using a two-photon laser as mentioned in the materials and methods. Propidium iodide staining (red) was used to visualize the nucleus (FIG. 8B), and differential interference contrast (DIC) was used to reveal the morphology of the cells. In both cell lines (MDA-MB-231 and MCF-7), VMY-1-103 localized into the cytoplasmic compartments. Similar results were found at different time intervals like 3, 6, 12 and 24 h (data was not shown). This supported the theory that VMY-1-103 binds to inactivate a form of Cdc2 in the cytoplasm, would be expected for an inducer of G2/M checkpoint. The cell lines were also treated with the drug for 48 hrs after which imaging was performed and it is clear that the morphology changes in the cell upon exposure to the drug. The drug treated cancer cells does not grow as well as in the control sample which indicates that the drug is inhibiting growth causing the cells to eventually die, See FIG. 4.

In order to see the binding ability of VMY-1-103 compare to dansyl ethylenediamine (fluorophore alone) on human breast tissue, the tissues were treated with 10 uM with corresponding compounds and imaged on two a photon microscope. As shown in the FIG. 8C, VMY-1-103 has strong affinity to binding to breast tissues compared to fluorophore alone. These results further confirmed that the activity is coming from the whole molecule not from individual fragments.

11. Example 11: Apoptotic Signaling

In order to understand whether VMY-1-101 and VMY-1-103 compounds were able to induce apoptotic cell death, the expression of anti- and pro-apoptotic proteins in MDA-MB-231 cells following treatment with 10 μM drugs for 48 hours was evaluated first. Western blot analysis of regulatory Bcl2, and Bax proteins for intrinsic apoptosis was shown in FIG. 7A. The data indicates that the decreased level of anti-apoptotic proteins and increased level of pro-apoptotic protein with compounds treated cells could imbalance the pro- and anti-apoptotic protein expression favoring apoptosis. This is further confirmed with proapoptotic 116 kDa poly (ADP-ribose) polymerase protein (PARP) into its 89-kDa fragments. As shown in the FIG. 7B VMY-1-101 and VMY-1-103 compounds undergoing moderate cleavage of the 116-kDa full length PARP into an 89-kDa fragment, a mechanism known to impair genomic integrity before apoptosis. The decrease in protein level of full length caspase 3 and 7 in VMY-1-101 and VMY-1-103 compound treated cells (data was not shown) was observed. Interestingly, there was no change in protein levels in roscovitine treated cells even at 40 μM. This was further supported by the present fluorescent compounds induces apoptosis mediated cell death in MDA-MB-231 cells unlike roscovitine.

To investigate the programmed cell death (apoptosis) in MCF-7 cells (caspase-3 negative), a biparametric cytofluorimetric analysis was performed, using propidium iodide (PI) and Annexin V-fluorescein isothiocyanate (FITC) which stain DNA and phosphatidylserine (PS) residues. Because externalization of PS occurs in the first stages of apoptosis, Annexin-V staining identifies apoptosis at an earlier stage than sub-G1 appearance. After 24 hour treatment with the compounds, MCF-7 cells were labeled with two dyes and monitored by flow cytometry. As shown in FIG. 7C, newly synthesized fluorescent compounds provoked a significant induction of apoptotic cells in both early and late apoptotic cell population after a 24 hour treatment at 10 μM. These findings further supports the present fluorescent compound treated cells were undergoing apoptotic cell death in MCF-7 cells.

a) Conclusion

Proper regulation of cell cycle division kinases (CDKs) is highly important for maintaining cell division in a correct fashion. Aberrant expression and activation of these proteins is a common feature in many cancers. Therefore CDKs are excellent targets for the design of anticancer agents. Several classes of CDK inhibitors including natural and chemical have been characterized but few are in clinical trails. A major problem in developing CDK-based drugs is non-specificity due to strong homologies of CDKs with other kinases. The majority of CDK inhibitors share the common feature i.e. binding to the ATP acceptor site of the kinases and subsequently inhibiting the catalytic activity of the enzymes. Besides selectivity, bio-distribution of CDK inhibitors poses another challenge and no efficient ways are available to monitor the biodistribution. To better understand the mechanistic pathways there is an urgent need to the development of trackable, selective and potent CDK analogs which would be useful in modulating and identifying CDKs. By taking advantage of the inherent fluorescence of the dansyl group, purvanalol B was chemically modified and two fluorescent derivatives were synthesized, which were potent fluorescent CDK inhibitors (FIG. 2A) These compounds were made employing a strategy of covalent attachment of a dansyl ethylenediamine group into purvanalol B and evaluating the in vitro antitumor behavior of novel compounds (VMY-1-101 and VMY-1-103) in two human adenocarcinoma cells, namely, p53-mutated and estrogen independent MDA-MB-231 cells and wild type p53, estrogen dependent MCF-7 cells. There activity was compared with already established CDK inhibitors, namely purvalanol B and Roscovitine.

Figure 2B:
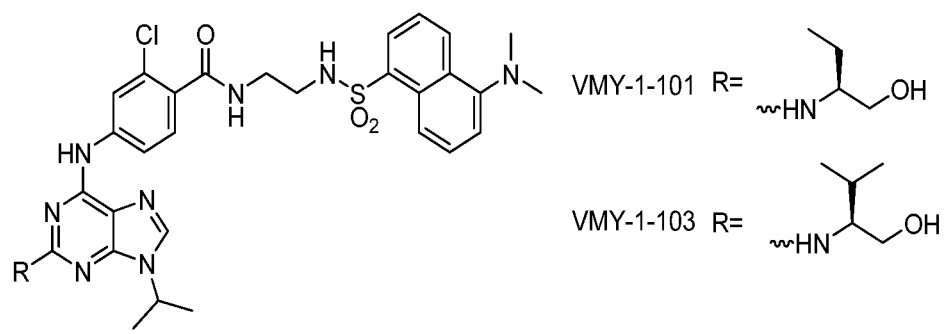
Figure 8B:
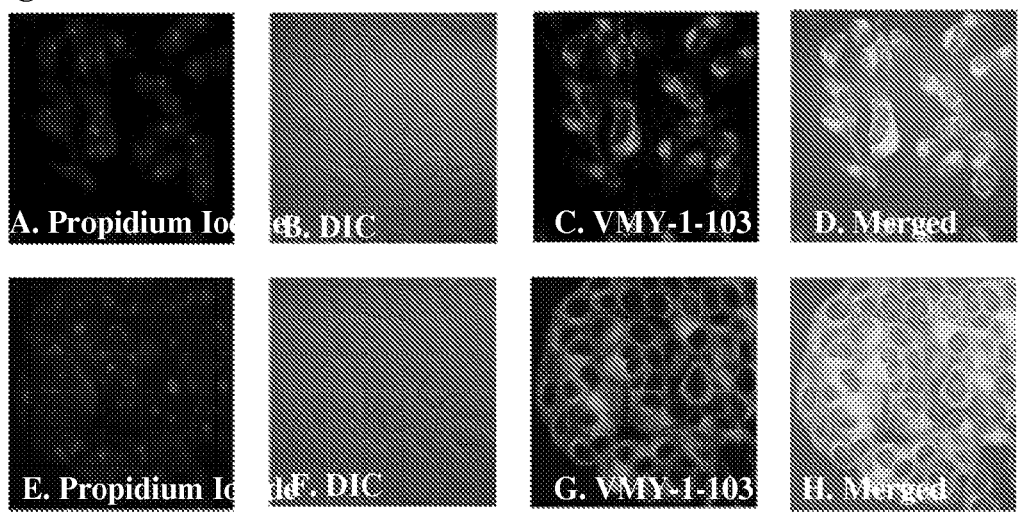
Figure 8C:
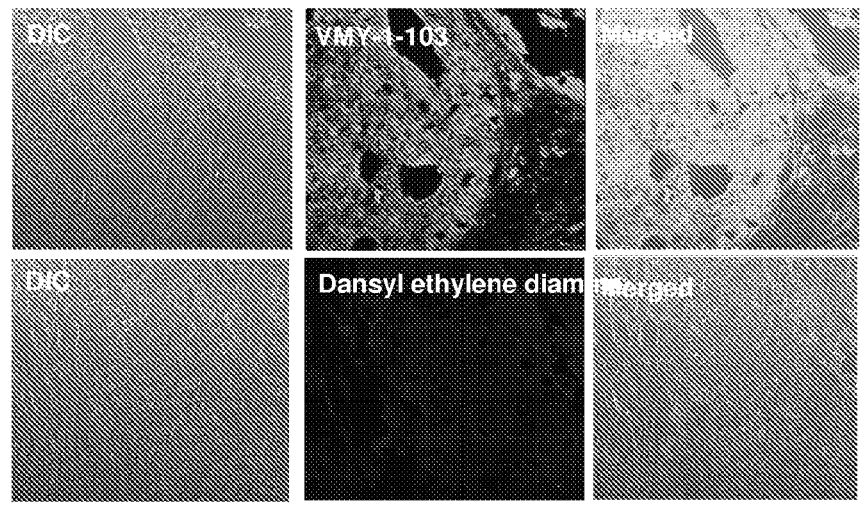

As shown in Table 2, the present fluorescent compounds showed the greatest activity against several CDK's involved in cell cycle control in particular CDK2/cyclin E (87 and 89% at 100 nM). Both compounds had potent antiproliferative activity ($IC_{50}$ 4-4.8 μM in MDA-MB-231 and 10-19 μM in MCF-7) irrespective of tissue of origin and compared to roscovitine by 13 fold in MDA-MB-231 cells and 2.8-5.5 fold in MCF-7 (Table 3). Morphological changes similar to dead cells induced by compounds VMY-1-101 and VMY-1-103 in both cell lines further support the potency towards anti-proliferative effects of fluorescent compounds as shown in FIG. 4. Treatment of breast tumor cell lines with compounds induces cell cycle arrest at G2/M phase, independent of estrogen status (FIG. 5). Interestingly, the VMY-1-103 compound showed irreversible antiproliferative effect compared to roscovitine (FIG. 6). From the therapeutic point of view, VMY-1-103 has greater clinical significance as it is not necessary to give a multiple dose to respond to tumor growth inhibition. In addition to that, VMY-1-103 has moderate activity in a multidrug resistance cell line and it is not a substrate for p-glycoprotein (Table 4). The inhibition of the expression level of phospho-CDC2 in MDA-MB-231 (FIG. 7), further supports that VMY-1-103 decreases the Cdc2 kinase activity, probably halting the cell division at the G2/M check point. Interestingly purvalanol B does not show any affect on expression of phosphor-Cdc2. The enhanced anti-proliferate activity of these fluorescent compounds over purvalanol B and Roscovitine could be accounted for the combination of two factors:

(1) increasing lipophilicity due to extra dansyl ethylenediamine group, increases the cell membrane permeability and (2) the increase in affinity of VMY-1-103 over purvalanol B likely from additional binding interactions (by such as hydrophobic and network of H-bonds) formed by extended substituent at chlorinated ring outside of the ATP binding pocket (FIG. 2B). Confocal images confirm the intracellular delivery of our CDK inhibitor (VMY-1-103) which localized in the cytoplasm of the human breast cancer cells (FIG. 8B). These further supported the interaction of VMY-1-103 with components (such as Cdc2 kinase) of mitosis, a cytoplasmic event.

Several apoptotic and cell survival parameters were modulated favoring apoptosis by these compounds. Down regulation of the anti-apoptotic (Bcl-2), up regulation of the pro-apoptotic proteins (Bax) proteins were observed indicating that our compounds induce apoptosis which were further confirmed by caspase-9 and caspase-3 cleavage, PARP cleavage (FIGS. 9A&B) and increase in Annexin-V positive cells indicating that the present class of fluorescent compounds induced apoptotic cell death (FIG. 9C).

12. Materials and Methods a) Cell Lines

The human breast adenocarcinoma cell lines MDA-MB-231 (HTB-26) and MCF-7 (HTB-22) were maintained in Dulbecco's modified Eagle's medium (DMEM) supplemented with 10% heat inactivated fetal bovine serum. (10%), 2 mM L-glutamine, and 50 μg/mL each of antibiotics, namely penicillin, streptomycin, and neomycin at 37° C. in a humidified incubator containing 5% $CO_2$ b) Test Compounds Roscovitine and purvalanol B were purchased from Sigma (St. Louis, Mo.) and VMY-1-101 and VMY-1-103 were prepared as described above. Drugs were dissolved in DMSO, stored at −20° C., and diluted in serum free medium immediately before use. All experiments were performed in 5% media c) Molecular Modeling Docking simulations was carried out using the program SurflexDock within Sybyl 8.2 program (Tripos Inc., St. Louis, USA) with the parameters are set to default, except the number of ligand conformations generation is set to 90. After consistent manual intervention of the best selected pose, a final model was arrived. The CDK2/VMY-1-103 complex structure was then refined by molecular dynamics simulation using the Amber 9 program suite (28) with the PARM98 force-field parameter. The charge and force field parameters of VMY-1-103 was obtained using the most recent Antechamber module in Amber 9 program, where VMY-1-103 was minimized at the MP2/6-31G* level. The SHAKE algorithm was used to keep all bonds involving hydrogen atoms rigid. Weak coupling temperature and pressure coupling algorithms were used to maintain constant temperature and pressure, respectively. Electrostatic interactions were calculated with the Ewald particle mesh method with a dielectric constant at $1R_{ij}$ and a nonbonded cutoff of 12 Å for the real part of electrostatic interactions and for VanderWaals interactions. Then the system was solvated in a 14 Å cubic box of water where the TIP3P model8 was used. 3000 steps of minimization of the system were performed in which CDK2 complex were constrained by a force constant of 100 kcal/mol/Å$^2$. After minimization, a 5 ps simulation was used to gradually raise the temperature of the system to 298 K while the complex was constrained by a force constant of 20 kcal/mol/Å. Another 10 ps of equilibration run was used where only the backbone atoms of the complex were constrained by a force constant of 5 kcal/mol/Å. Final production run of 50 ps was performed with no constraints. When applying constraints, the initial complex structure was used as a reference structure. The PME method was used and the time step was 5 fs, and neighboring pairs list was updated in every 30 steps.

d) Kinase Assay

Kinase selectivity of compounds VMY-1-101 and VMY-1-103 were screened at Millipore, Dundee, UK. Briefly assays were performed with a Biomek 2000 Laboratory Automation Workstation in a 96-well format (Beckman instruments, Palo Alto, Calif., U.S.A) for 40 min at ambient temperature in 25 μL incubations using [γ-$^{33}$P]-ATP. In a final reaction volume of 25 μL corresponding CDK/cyclin (h) (5-10 mU) was incubated with 8 mM MOPS pH 7.0, 0.2 mM EDTA, 0.1 mg/mL histone H1, 10 mM MgAcetate and [γ-$^{33}$P-ATP](specific activity approx. 500 cpm/pmol, concentration as required). The reaction was initiated by the addition of the MgATP mix. After incubation for 40 min at room temperature, the reaction was stopped by the addition of 5 μL of a 3% phosphoric acid solution. From the reaction, 10 μL was spotted onto a P30 filtermat and washed three times for 5 minutes in 75 mM phosphoric acid and once in methanol prior to dying and scintillation counting.

e) Cell Viability Assay (WST-1)

Briefly human breast cancer cells were seeded into a 96-well plate at 3000 cells per well in DMEM containing 10% FBS. Following 24 hours attachment period, compounds were dissolved in DMSO and serially diluted in tissue culture media and added to the cells in triplicate, and incubated for 48 h at 37° C. Control cells were treated with equal amount of DMSO. After 48 h incubation, cell viability was measured by WST-1 assay according to the manufacturer's instructions (Roche). Briefly, 20 μL of WST-1 solution was added in each well and incubated for 2-3 hours. The water soluble tetrazolium salt of WST-1 is converted into orange formazan by dehydrogenase in the mitochondria of living cells. The formazan absorbance, which correlates to the number of living cells, was measured at 450 nm and 630 nm as reference filter using a microplate reader. (Ultramark, Microplate Imaging System, Bio-Rad). The $IC_{50}$ was calculated from the graph of the log of the compound concentration versus the fraction of the surviving cells.

f) Cell Cycle Analysis

The effect of CDK inhibitors on cell cycle progression was analyzed by flow cytometry. Cells were treated with 5 μM and 10 μM Compounds, Purvalanol B or Rosovitine for 24 hours. Cells were trypsinized, centrifuged (2000 rpm) and cell pellets were collected. Pellets were washed with 1×PBS, permeabilized with 70% (v/v) ethanol, resuspended in 1 ml of PBS containing 1 mg/ml Rnase and 50 mg/ml propidium iodide, incubated in the dark for 30 min at room temperature, and analysed by a FACSort Flow Cytometer (Becton Dickinson, San Jose, Calif.). The cell cycle distribution was evaluated on DNA plots using the Modfit software (Verity softwarehouse, Topsham, Me.).

g) Western Blot Analysis

Western blotting was performed according to literature procedure. In brief, cell pellets were collected at the indicated times after treatment with compounds, suspended in 100 μL of lysis buffer (50 mM Tris-HCl, 150 mM NaCl, 1 mM EGTA, 1 mM EDTA, 20 mM NaF, 100 mM Na3VO4, 0.5% NP-40, 1% Triton X-100, 1 mM PMSF, 5 μg/ml aprotinin, 5 μg/ml leupeptin), vortexed twice and incubated in an ice bath for 30 min. Lysates were cleared by centrifugation at 12000 rpm for 15 min at 4° C. and protein was estimated by detergent compatible BCA protein assay kit (Pierce). Equivalent amounts of total proteins were resolved by SDS-PAGE (10%) and transferred to PVDF membrane. Membranes were blocked by 5% non-fat powdered milk in TBST overnight.

Membranes were incubated with indicated primary antibodies for 2 hours followed by HRP-conjugated secondary antibodies for 1 hr and developed using enhanced chemiluminescence kit (Perkin Elmer).

h) Annexin V Binding Assay

Loss of phospholipid asymmetry of the plasma membrane is an early event of apoptosis (33, 34). The annexin V binding assay was performed according to the protocol (BD Pharmingen™) to detect the early event of apoptosis, cells were washed twice with cold PBS and then resuspended in 1× binding buffer at a concentration of 1×10$^6$ cells/ml. 100 µl of the solution was transferred to a 5 µl culture tube and a 5 µL of Annexin V-FITC was added followed by 5 µL of PI. Cells were vortexed gently and incubated for 15 min at RT in the dark. Immediately after adding 400 µL of 1× binding buffer to each tube, cells were analyzed by FCSort Flow Cytometer (Becton Dickinson, San jose, CA) and data were analyzed using FCSExpress Denovo software (Los Angeles, Calif.). Viable cells were FITC−/PI−, apoptotic cells were FITC+/PI−, and necrotic cells were FITC+/PI+.

i) Distribution of Breast tissue

Breast tissues were subjected auto shaker program 7 for de-wax and re-hydration, epitode retrieval for 20 min at 100° C. in steamer, 20 min cooling at RT. Tissue were block in 10% goat serum 10 min at RT, exposed 5% goat-serum 2 hours at RT and finally washed two times with distilled water. After epitode retrieval of breast tissues exposed to 10 µM of VMY-1-103 and Dansyl ethylenediamine for 1 h at room temperature, washed with two times with distilled water for 5 min and mount in aquamount. Images were taken with multiphoton confocal microscopy X63 oil immersion (Zeiss510LSM/META/NLO live imaging) at excitation 720 nm and the absorbance was read with a band path filter of 480-520 nm.

j) Confocal Microscopy

Cells were seeded at a density of 5×10$^5$ on sterilized microscope slides coated with poly-D-lysine. After 24 h incubation, slides were washed with serum free medium, treated with 10 µM of VMY-1-103 for 1 h. Cells were washed twice with PBS, fixed with 4% formaldehyde in PBS for 15 min at room temperature and washed again with PBS. For nuclear staining cells were incubated with propidium iodide for 5 min and washed with PBS and finally mounted on glass slides using Antifade solution. Images were taken with multiphoton confocal microscopy X63 oil immersion (Zeiss510LSM/META/NLO live imaging) at excitation 720 nm and the absorbance was read with a band path filter of 480-520 nm.

What is claimed is:

1. A method for synthesizing roscovitine and purvalanol analogs, comprising the steps of: a) providing 2-fluoro-6-chloro-purine; b) functionalizing the N$_9$ position of the purine with a C$_{1-4}$ alkyl group; c) providing a small aromatic or small heteroaromatic ring system that is substituted with an amino group and with a protected or unprotected group selected from the moieties consisting of carboxylic acid, amide, sulfamide and phosphamide; d) adding the amino group of the small aromatic or small heteroaromatic ring system to the purine C$_6$ position; e) condensing the protected or unprotected group with a linker that is a side chain on a fluorophore moiety, wherein the linker is alkyl, alkenyl, alkynyl, polyalkylamine, alkylene polyamine, sulfoester, phosphoester, amide, sulfamide, or phosphoamide; and f) adding an optionally substituted hydrocarbon amine at the purine C$_2$ position.

2. The method according to claim 1 wherein the ring system is provided in the form of 4-amino-2-chloro-benzoic acid, 4-amino-benzoic acid, 4-aminomethyl-benzoic acid, or 4-aminomethyl-2-chloro-benzoic acid.

3. The method according to claim 1, wherein the linker has 8 backbone atoms or less.

4. The method according to claim 1, wherein the fluorophore moiety comprises dansyl and the linker comprises ethylene diamine.

5. A method for synthesizing roscovitine and purvalanol analogs, comprising the steps of: a) providing 2-fluoro-6-chloro-purine; b) functionalizing the N$_9$ position of the purine with a C$_{1-4}$ alkyl group; c) providing a small aromatic or small heteroaromatic ring system that is substituted with an amino group and with a protected or unprotected group selected from the moieties consisting of carboxylic acid, amide, sulfamide and phosphamide; d) adding the amino group of the small aromatic or small heteroaromatic ring system to the purine C$_6$ position; e) condensing the protected or unprotected group with a linker, wherein the linker is alkyl, alkynyl, polyalkylamine, alkylene polyamine, sulfoester, phosphoester, amide, sulfamide, or phosphoamide, wherein the linker does not comprise a fluorophore, f) adding an optionally substituted hydrocarbon amine at the purine C$_2$ position.

6. The method according to claim 5, wherein the ring system is provided in the form of 4-amino-2-chloro-benzoic acid, 4-amino-benzoic acid, 4-aminomethyl-benzoic acid, or 4-aminomethyl-2-chloro-benzoic acid.

7. The method according to claim 5, wherein the linker contains a reactive moiety, wherein the reactive moiety is a nucleophile, or a moiety susceptible to nucleophilic attack.

8. A compound produced by the method of claim 1.

9. A compound, wherein the compound is roscovitine analog or a purvalanol analog, wherein the analog comprises at the N$_9$ position of the purine a C$_{1-4}$ alkyl group; at the C$_6$ of the purine a small amino substituted aromatic or small heteroaromatic ring system, further substituted with a moiety selected from the group consisting of carboxylic acid, amide, sulfamide and phosphamide attached to a linker, wherein the linker is attached to a fluorophore moiety.

10. The compound according to claim 9, wherein the ring system comprises 4-amino-2-chloro-benzoic acid, 4-amino-benzoic acid, 4-aminomethyl-benzoic acid, or 4-aminomethyl-2-chloro-benzoic acid.

11. The compound of claim 9, wherein the linker is alkyl, alkenyl, alkynyl, polyalkylamine, alkylene polyamine, sulfoester, phosphoester, amide, sulfamide, or phosphoamide.

12. A method of labeling a cell, comprising incubating a fluorescently labeled molecule with the cell, wherein the fluorescently labeled molecule is a compound of claim 9, wherein the fluorescently labeled molecule specifically interacts with a protein present in the cell, wherein the incubating occurs in conditions allowing interaction of fluorescently labeled molecule with the protein.

13. A method of detecting a tumor cell comprising incubating a potential tumor cell with a compound, wherein the compound is a compound of claim 9, wherein the compound interacts with a protein on a tumor cell, wherein the presence or absence of the protein in the cell indicates it is related to a tumor cell, wherein the compound comprises a fluorescent moiety, and identifying the association of fluorescence with the potential tumor cell.

14. A compound, wherein the compound is roscovitine analog or a purvalanol analog, wherein the analog comprises at the N$_9$ position of the purine a C$_{1-4}$ alkyl group; at the C$_6$ of the purine a small amino substituted aromatic or small heteroaromatic ring system, further substituted with a moiety selected from the group consisting of carboxylic acid, amide, sulfamide, and phosphamide attached to a linker, wherein the linker is attached to a fluorophore moiety, wherein the fluorophore moiety comprises dansyl and the linker comprises ethylene diamine.

15. A compound, wherein the compound is roscovitine analog or a purvalanol analog, wherein the analog comprises at the $N_9$ position of the purine a $C_{1-4}$ alkyl group; at the $C_6$ of the purine a small amino substituted aromatic or small heteroaromatic ring system, further substituted with a moiety selected from the group consisting of carboxylic acid, amide, sulfamide and phosphamide attached to a linker, wherein the linker is alkyl, alkynyl, polyalkylamine, sulfoester, phosphoester, amide, sulfamide, or phosphoamide, wherein the linker does not comprise a fluorophore, and at the $N_2$ position of the purine a 2-yl-1-butanol or 2-yl-3-methyl-1-butanol group.

16. The compound according to claim 15, wherein the ring system comprises 4- amino-2-chloro-benzoic acid, 4-amino-benzoic acid, 4-aminomethyl-benzoic acid, or 4-aminomethyl-2-chloro-benzoic acid.

17. The compound according to claim 15, wherein the linker has 8 backbone atoms or less.

\* \* \* \* \*